(12) United States Patent
Byrd et al.

(10) Patent No.: US 9,044,474 B2
(45) Date of Patent: Jun. 2, 2015

(54) COMPOSITIONS AND METHODS FOR INCREASING DRUG EFFICACY IN CANCER

(75) Inventors: John C. Byrd, Columbus, OH (US);
Amy J. Johnson, Columbus, OH (US);
Emilia Mahoney, Columbus, OH (US);
David M. Lucas, Hilliard, OH (US);
Michael R. Grever, Powell, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/883,862

(22) PCT Filed: Nov. 7, 2011

(86) PCT No.: PCT/US2011/059645
§ 371 (c)(1),
(2), (4) Date: Jul. 15, 2013

(87) PCT Pub. No.: WO2012/064671
PCT Pub. Date: May 18, 2012

(65) Prior Publication Data
US 2014/0005250 A1    Jan. 2, 2014

Related U.S. Application Data

(60) Provisional application No. 61/411,236, filed on Nov. 8, 2010.

(51) Int. Cl.
| | | |
|---|---|---|
| *C12N 15/11* | (2006.01) | |
| *C12N 9/99* | (2006.01) | |
| *A61K 31/4706* | (2006.01) | |
| *G01N 33/574* | (2006.01) | |
| *A61K 45/06* | (2006.01) | |
| *A61K 31/343* | (2006.01) | |
| *A61K 31/453* | (2006.01) | |
| *A61K 48/00* | (2006.01) | |

(52) U.S. Cl.
CPC ...... *A61K 31/4706* (2013.01); *G01N 33/57426* (2013.01); *G01N 2800/52* (2013.01); *A61K 45/06* (2013.01); *A61K 31/343* (2013.01); *A61K 31/453* (2013.01); *A61K 48/005* (2013.01)

(58) Field of Classification Search
CPC .............. A61K 2039/00; A61K 2267/035; C07K 2316/00; C07K 16/00; C07K 1/00
See application file for complete search history.

(56) References Cited

U.S. PATENT DOCUMENTS

| | | | |
|---|---|---|---|
| 6,316,435 B2 | 11/2001 | Byrd et al. | |
| 6,841,565 B1 | 1/2005 | Lucas et al. | |
| 2001/0006974 A1 | 7/2001 | Byrd et al. | |
| 2002/0016293 A1* | 2/2002 | Ratain et al. | 514/9 |
| 2005/0191632 A1 | 9/2005 | Byrd et al. | |
| 2008/0027105 A1 | 1/2008 | Suarez et al. | |
| 2009/0226429 A1* | 9/2009 | Salcedo et al. | 424/133.1 |
| 2010/0022655 A1 | 1/2010 | Byrd et al. | |
| 2010/0256072 A1 | 10/2010 | Perrotti et al. | |
| 2010/0272636 A1 | 10/2010 | Byrd et al. | |
| 2011/0251240 A1 | 10/2011 | Suarez et al. | |

OTHER PUBLICATIONS

Fujiwara et al, Pivotal Role of the Cyclin-Dependent Kinase Inhibitor p21 WAF1/CIP1 in Apoptosis and Autophagy, 2008, J.Biol.Chem. 283: 388-397.*
Byrd et al, Flavopiridol Induces Apoptosis in Chronic Lymphocytic Leukemia Cells Via Activation of Caspase-3 Without Evidence of bcl-2 Modulation or Dependence on Functional p53, 1998, Blood, vol. 92, 10: 3804-3816.*
Fujiwara et al., "Pivotal Role of the Cyclin-dependent Kinase Inhibitor p21WAF1/CIP1 in Apoptosis and Autophagy," The Journal of Biological Chemistry, 2008, vol. 283, No. 1, pp. 388-398.
Venkat, "Flavopiridol: A Drug that May Save Lives," National Cancer Institute, Jun. 6, 2004.

* cited by examiner

*Primary Examiner* — Tracy Vivelmore
*Assistant Examiner* — Kate Poliakova-Georgantas
(74) *Attorney, Agent, or Firm* — MacMillan, Sobanski & Todd, LLC

(57) ABSTRACT

A method of (a) treating a lymphoproliferative disease in a subject in need thereof; (b) slowing the progression of lymphoproliferative disease in a subject who has been diagnosed with a lymphoproliferative disease; or (c) preventing or delaying development of a lymphoproliferative disease in a subject who is at risk of developing a lymphoproliferative disease. The method generally comprises administering to the individual an effective amount of a combination therapy comprising: i) at least one autophagy modulating agent, or a derivative, pharmaceutically acceptable salt thereof, or prodrug thereof; and ii) at least one CDK inhibitor agent, or a derivative, pharmaceutically acceptable salt thereof, or prodrug thereof, wherein the i) agent and the ii) agents are administered in amounts sufficient to enhance the cytotoxicity of the combination relative to the CDK inhibitor agent treatment alone.

10 Claims, 26 Drawing Sheets
(8 of 26 Drawing Sheet(s) Filed in Color)

COMPOSITIONS AND METHODS FOR INCREASING DRUG EFFICACY IN CANCER

CROSS-REFERENCE TO RELATED APPLICATIONS

This is a national stage application filed under 37 CFR 1.371 of international application PCT/US2011/059645 filed Nov. 7, 2011, which claims the priority to U.S Provisional Application No. 61/411,236 filed Nov. 8, 2010, the entire disclosures of which are expressly incorporated herein by reference.

STATEMENT REGARDING FEDERALLY SPONSORED RESEARCH

This invention was made with government support under Grant No. PO1 CA81534-11 awarded by the National Cancer Institute. The government has certain rights in the invention.

BACKGROUND OF THE INVENTION

There is no admission that the background art disclosed in this section legally constitutes prior art.

Chronic lymphocytic leukemia (CLL) is a progressive B-cell malignancy that demonstrates significant heterogeneity with respect to biology as well as progression-free and overall survival. Due to the lack of survival advantage with early treatment, therapy for CLL is delayed until symptoms develop. Therapeutic regimens for symptomatic CLL have improved significantly over the past decade with introduction of combination therapies that include nucleoside analogs and monoclonal antibodies (chemoimmunotherapy), and for the first time, prolongation of survival is being observed. Unfortunately, even these new chemoimmunotherapy strategies are not curative, and virtually all CLL patients will eventually relapse and succumb to their disease. The lack of curative and effective therapy for all genetic subsets of CLL has fueled investigation of new therapeutic approaches for this disease.

Cyclin-dependent kinases (CDKs) are important regulators that control the timing and coordination of the cell cycle. CDKs form reversible complexes with their obligate cyclin partners to control transition through key junctures in the cell cycle. Endogenous cyclin dependent kinase inhibitory proteins (CDKIs) are known that bind either the CDK or cyclin component and inhibit the kinase activity. Flavopiridol, (cis-5,7-dihydroxy-2-(2-chlorophenyl)-8-[4-(3-hydroxy-1-methyl)-piperidin-yl]-1-benzopyran-4-one)hydrochloride is a synthetic flavone that has been shown to be a potent and selective inhibitor of the CDKs, and its antitumor activity is related to its CDK inhibitory activity. However, despite promising pre-clinical studies with the cyclin-dependent kinase inhibitor flavopiridol in relapsed chronic lymphocytic leukemia (CLL) and other diseases, previous clinical trials with this agent have been disappointing.

There is clinical evidence that the presence or absence of one or more cytogenetic abnormalities impact the response to various CLL treatments, which in turn influences patient survival and quality of life. Medical professionals would be better equipped to make treatment decisions regarding CLL if they could understand and predict the likely therapeutic response or resistance of the disease to treatment in a particular patient. Accordingly, there is a need for methods and systems which enable the identification of cytogenetic abnormalities that are predictive of response of CLL cells in a patient to one or more treatments or therapeutic agents. Such methods and systems would permit customization of treatment for CLL based on the particular genetic makeup of each patient.

Accordingly, there still remains room for improvement in the treatment of chronic lymphocytic leukemia, and other lymphoproliferative diseases. Accordingly, there is a need for improvement in treating lymphoproliferative diseases.

SUMMARY OF THE INVENTION

In a first broad aspect, there is provided herein a method of (a) treating a lymphoproliferative disease in a subject in need thereof; (b) slowing the progression of lymphoproliferative disease in a subject who has been diagnosed with a lymphoproliferative disease; or (c) preventing or delaying development of a lymphoproliferative disease in a subject who is at risk of developing a lymphoproliferative disease.

The method generally comprises administering to the individual an effective amount of a combination therapy comprising:

i) at least one autophagy modulating agent, or a derivative, pharmaceutically acceptable salt thereof, or prodrug thereof; and ii) at least one CDK inhibitor agent, or a derivative, pharmaceutically acceptable salt thereof, or prodrug thereof, wherein the i) agent and the ii) agents are administered in amounts sufficient to enhance the cytotoxicity of the combination relative to the CDK inhibitor agent treatment alone.

In certain embodiments, administration of the i) agent enhances the therapeutic effect of the ii) agent compared to administration of the ii) agent in the absence of the i) agent.

In certain embodiments, the ii) agent is administered in a dosage amount that is less than that required for the ii) agent as an individual therapy to elicit a comparable therapeutic effect.

In another broad aspect, there is provided herein a pharmaceutically acceptable composition comprising: i) at least one autophagy modulating agent, or a derivative, pharmaceutically acceptable salt thereof, or prodrug thereof; and ii) at least one CDK inhibitor agent, or a derivative, pharmaceutically acceptable salt thereof, or prodrug thereof.

In certain embodiments, the i) agent and the ii) agent are in a single unit dosage form.

In another broad aspect, there is provided herein a kit comprising: i) at least one autophagy modulating agent, a derivative, pharmaceutically acceptable salt thereof, or prodrug thereof; and ii) at least one cyclin-dependent kinase inhibitor agent, a derivative, pharmaceutically acceptable salt thereof, or prodrug thereof.

In another broad aspect, there is provided herein a kit comprising: i) at least one autophagy modulating agent, or a derivative, pharmaceutically acceptable salt thereof, or prodrug thereof; and ii) at least one CDK inhibitor agent, or a derivative, pharmaceutically acceptable salt thereof, or prodrug thereof; and, iii) instructions for use of in the treatment, prevention, slowing the progression or delaying the onset and/or development of a lymphoproliferative disease.

In another broad aspect, there is provided herein a method of treating a lymphoproliferative disease in an individual in need thereof comprising administering to an individual a combination therapy, the combination therapy comprising: i) at least one autophagy modulating agent, a derivative, pharmaceutically acceptable salt thereof, or prodrug thereof; and ii) at least one CDK inhibitor agent, a derivative, pharmaceutically acceptable salt thereof, or prodrug thereof; wherein the combination therapy is administered in an amount effective to improve a symptom of lymphoproliferative disease and wherein the combination therapy elicits improvement to a greater extent than use of the ii) agent in the absence of the i) agent.

In certain embodiments, the i) agent and the ii) agent are administered simultaneously, separately or sequentially.

In certain embodiments, the method comprises administering the ii) agent in an amount effective to obtain a therapeutic effect, and the i) agent in an amount effective to block any adverse effects mediated by the ii) agent, but not to antagonize the therapeutic effect of the ii) agent.

In certain embodiments, the method comprises treating a cancer patient.

In certain embodiments, the subject is refractory to other treatments.

In certain embodiments, the subject is a human subject.

In another broad aspect, there is provided herein a method of inhibiting tumor growth in a cancer patient comprising administering to the patient a combination therapy comprising effective amounts of: i) at least one autophagy modulating agent, a derivative, pharmaceutically acceptable salt thereof, or prodrug thereof; and ii) at least one CDK inhibitor agent, a derivative, pharmaceutically acceptable salt thereof, or prodrug thereof, wherein the i) agent substantially reduces the toxic side effects of the ii) agent.

In another broad aspect, there is provided herein a method of treating a subject having chronic lymphocytic leukemia (CLL), comprising treating the subject with a combination of: i) at least one autophagy modulating agent, a derivative, pharmaceutically acceptable salt thereof, or prodrug thereof; and ii) at least one CDK inhibitor agent, a derivative, pharmaceutically acceptable salt thereof, or prodrug thereof, in an amount sufficient to enhance the cytotoxicity of the combination relative to the CDK inhibitor agent treatment alone.

In another broad aspect, there is provided herein a use of CDK inhibitor agents to promote endoplasmic reticulum (ER) stress, and also identify autophagy as a mechanism of CDK inhibitor agent resistance that can be therapeutically targeted in resistant tumors.

In another broad aspect, there is provided herein a method for treating a flavopiridol-resistant cell, comprising administering an effective amount of at least therapeutic agent (chloroquine) that blocks the autophagic process in the flavopiridol-resistant cell.

In another broad aspect, there is provided herein a method for interfering with autophagy in cells in need thereof, comprising targeting one or more of ATG4 members and the Vps34/Beclin1/Barkor complex in such cells.

In another broad aspect, there is provided herein a use of a combination therapy for targeting autophagy and UPR networks in the treatment of cancer. The endoplasmic reticulum (ER) is a multi-functional cellular compartment that functions in protein folding, lipid biosynthesis, and calcium homeostasis. Perturbations in ER function cause dysregulation of ER homeostasis and accumulation of misfolded and unfolded proteins in the organelle, leading to ER stress. Cells cope with ER stress by activating an ER stress signaling network, also called the Unfolded Protein Response (UPR). It is to be understood the "unfolded protein response" (UPR) is now believed to be triggered by the presence of misfolded protein in the ER, and includes three components that counteract ER stress: gene expression, translational attenuation, and ER-associated protein degradation (the ERAD system).

In another broad aspect, there is provided herein a method of treating lymphoproliferative diseases in a subject, comprising (co)administering to the subject a therapeutic combination comprising: i) at least one autophagy modulating agent, a derivative, pharmaceutically acceptable salt thereof, or prodrug thereof; and ii) at least one CDK inhibitor agent, a derivative, pharmaceutically acceptable salt thereof, or prodrug thereof, in an amount sufficient to enhance the cytotoxicity of the combination relative to the CDK inhibitor agent treatment alone.

In certain embodiments, at least i) agent is (co)administered in an amount ranging from about 0.1 μM to about a maximum tolerated dosage for the i) modulating agent.

In certain embodiments, the i) agent is (co)administered in an amount ranging from about 0.1 to about 0.5 μM.

In certain embodiments, the combination is (co)administered parenterally, orally, intraperitoneally, intravenously, intraarterially, transdermally, intramuscularly, liposomally, via local delivery by catheter or stent, subcutaneously, intraadiposally, or intrathecally.

In certain embodiments, the therapeutic combination is (co)administered intravenously.

In certain embodiments, the lymphoproliferative disease comprises low-grade lymphoproliferative disorders, chronic lymphocytic leukemias, cutaneous T cell leukemias, Sezary syndrome, hairy cell leukemias, lymphomas, Non-Hodgkin's lymphomas, and large granular lymphocytic leukemias.

In certain embodiments, the lymphoproliferative disease comprises chronic lymphoproliferative diseases.

In another broad aspect, there is provided herein a marker for determining effectiveness of flavopiridol as a therapeutic treatment for a subject having chronic lymphocytic leukemia (CLL), comprising detecting an increased expression of cytoplasmic LC3 protein.

In another broad aspect, there is provided herein a method for increasing the efficacy of flavopiridol treatment in a subject having chronic lymphocytic leukemia (CLL), comprising administering an effective amount of chloroquine in as amount sufficient to reduce autophagy in the subject.

In another broad aspect, there is provided herein a method for increasing the efficacy of flavopiridol treatment in a subject having chronic lymphocytic leukemia (CLL), comprising administering an effective amount of an ATG member antagonist (i.e., ATG 4, 5, 8) in an amount sufficient to reduce autophagy in the subject.

In another broad aspect, there is provided herein a method for increasing the efficacy of a ER stress treatment inducing treatment a subject having chronic lymphocytic leukemia (CLL), comprising administering an effective amount of an ATG member antagonist (i.e., ATG 4, 5, 8) or chloroquine in as amount sufficient to reduce autophagy in the subject.

In another broad aspect, there is provided herein a method of enhancing an individual's response to a chemotherapeutic agent comprising, administering: i) at least one autophagy modulating agent in connection with the chemotherapeutic agent, wherein the individual has or is suspected of having a lymphoproliferative disease.

In another broad aspect, there is provided herein a method of modulating autophagy in a cell in need thereof, comprising potentiating at least one CDK inhibitor in the cell by administering an effective amount of at least one CDK inhibitor agent, a derivative, pharmaceutically acceptable salt thereof, or prodrug thereof.

In another broad aspect, there is provided herein an agent that inducing ER stress (thapsigargen, flavopiridol, others) have autophagy as a mechanism of resistance and targeting autophagy for these will enhance killing In another broad aspect, there is provided herein an agent for potentiating the antitumor effect of at least one CDK inhibitor agent, containing at least one autophagy modulating agent, or a derivative, pharmaceutically acceptable salt thereof, or prodrug thereof, in effective amount for the antitumor effect of the at least one CDK inhibitor agent being significantly potentiated.

In another broad aspect, there is provided herein a use of i) at least one autophagy modulating, or a derivative, pharmaceutically acceptable salt thereof, or prodrug thereof, and ii) at least one CDK inhibitor agent, or a derivative, pharmaceutically acceptable salt thereof, or prodrug thereof, in combination, for producing an antitumor agent.

In another broad aspect, there is provided herein a method for treating cancer, comprising administering: i) at least one autophagy modulating agent, or a derivative, pharmaceutically acceptable salt thereof, or prodrug thereof; and ii) at least one CDK inhibitor agent, or a derivative, pharmaceutically acceptable salt thereof, or prodrug thereof, to a patient in need thereof in combination In certain embodiments, the method for treating cancer includes wherein: i) at least one autophagy modulating agent, or a derivative, pharmaceutically acceptable salt thereof, or prodrug thereof; and ii) at least one CDK inhibitor agent, or a derivative, pharmaceutically acceptable salt thereof, or prodrug thereof, are administered to a patient in need thereof simultaneously, or separately at an interval.

In another broad aspect, there is provided herein a method for potentiating antitumor effect of: ii) at least one CDK inhibitor agent, or a derivative, pharmaceutically acceptable salt thereof, or prodrug thereof, the method comprising:

administering i) at least one autophagy modulating agent, or a derivative, pharmaceutically acceptable salt thereof, or prodrug thereof; to a patient to which the ii) agent is administered, in effective amount for the antitumor effect of the ii) agent being significantly potentiated.

In another broad aspect, there is provided herein a method of treating a lymphoproliferative disease in a subject in need of such a treatment, the method comprising administering: i) at least one autophagy modulating agent, or a derivative, pharmaceutically acceptable salt thereof, or prodrug thereof; in a combination therapy with one or more chemotherapeutic agents, wherein the i) agent is administered in amounts effective in potentiating the action of the chemotherapeutic agent or agent.

In another broad aspect, there is provided herein a method of enhancing autophagy in one or more mammalian cells, comprising contacting the one or more cells with at least one CDK inhibitor and at least one: at least one autophagy modulating agent, or a derivative, pharmaceutically acceptable salt thereof, or prodrug thereof; wherein the at least one CDK inhibitor and the at least one agent are in an amount sufficient to enhance autophagy in the one or more cells.

In another broad aspect, there is provided herein a method of enhancing a therapeutic agent that causes an autophagic mechanism of resistance in a cell, the method comprising administering: i) at least one autophagy modulating agent, or a derivative, pharmaceutically acceptable salt thereof, or prodrug thereof; in an amount sufficient to overcome such mechanism of resistance.

In another broad aspect, there is provided herein a pharmaceutical composition comprising an autophagy inducing compound in an amount effective for treating an autophagy associated disease, wherein the compound comprises chloroquine.

In certain embodiments, wherein the composition further comprises a pharmaceutically acceptable carrier.

In another broad aspect, there is provided herein a method of inducing autophagy in a cell, the method comprising contacting the cell with an autophagy inducing compound in an amount effective to induce autophagy in the cell, wherein the autophagy inducing compound comprises chloroquine or bafilomycin.

In another broad aspect, there is provided herein a method of causing an effect in a cell, wherein the effect is selected from the group consisting of: inducing ER stress in a cell, inducing autophagy in a cell, and inhibiting cyclin-dependent kinase activity in a cell, the method comprising administering to the cell an effective dose of the combination therapy comprised of the i) agent and the ii) agent of any one of the claims above, wherein administration of the effective dose to the cell will cause the effect in the cell.

In certain embodiments, the cell is under low levels of endoplasmic reticulum (ER) stress prior to administration of the combination therapy.

In certain embodiments, the cell is present in a subject.

In certain embodiments, the cell is present in an in vitro cell culture.

In certain embodiments, the cell is a human cell.

In certain embodiments, the cell is a cancer cell.

In certain embodiments, the cell is an in vivo cancer cell.

In certain embodiments, the cell is an in vitro cancer cell.

In another broad aspect, there is provided herein a method of reducing viability of a tumor cell in a subject, comprising:

a) introducing into a tumor cell in the subject an agent effective to modulate endoplasmic reticulum (ER) stress response and sensitize the tumor cell to the therapeutic activity of an anticancer agent in the subject; and b) contacting the tumor cell with the anticancer agent in an amount effective to reduce viability of the sensitized tumor cell, wherein viability of the tumor cell is reduced.

In certain embodiments, the agent is effective to enhance, diminish or inhibit the ER stress response in the subject.

In certain embodiments, the agent is a siRNA specific to at least one of the ATG family members, ATG4 members and the Vps34/Beclin1/Barkor complex.

In certain embodiments, the tumor cell or cancer cell is selected from , bladder cancer, breast cancer, colon cancer, glioblastoma, liver cancer, lung cancer, lymphoma, neck and mouth cancer, ovarian cancer cells, prostate cancer, pancreatic cancer, and renal cell cancer.

In another broad aspect, there is provided herein a method of sensitizing a tumor or cancer cell to cytolytic activity of an anticancer agent, the method comprising inducing in a subject a mild stress to the endoplasmic reticulum (ER).

In certain embodiments, inducing the mild stress comprises genetically disrupting an ER stress response gene.

In certain embodiments, the ER stress response gene is selected from the group consisting of to at least one of the ATG family members, ATG4 members and the Vps34/Beclin1/Barkor complex.

In another broad aspect, there is provided herein a method of treating a subject having a condition associated with endoplasmic reticulum (ER) stress-related cell death, the method comprising: selecting a subject in need of such treatment; and administering to the subject a therapeutically effective amount of the combination therapy of any one of the above claims, comprised of the i) agent and the ii) agent; thereby treating the subject.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs.

Copies of this patent or patent application publication with color drawing(s) and/or photograph(s) will be provided by the U.S. Patent and Trademark Office upon request and payment of the necessary fees.

FIG. 1A: Confocal fluorescence microscopy for CLL cells untreated or after 4 hours starvation in HBSS or 4 hours treatment with rapamycin (5 µM) or thapsigargin (1 µM). LC3 (red) shows autophagosomes, Lamp2 (green) shows lysosomes, DAPI (blue) shows nuclei. Images were collected with 60× objective and 4× optical zoom.

FIG. 1B: Quantification of LC3 immunofluorescence intensity. Integrated intensity was averaged in 5 microscopic fields relative to number of cells per field, and then averaged in 6 CLL patients' cells. Differences from vehicle-treated were significant (P<0.0001).

FIG. 1C: Immunoblot for LC3B I and II in CLL cells (representative of 4 experiments). GAPDH was used as loading control.

FIG. 2A: Confocal fluorescence microscopy of CLL cells incubated 4 hours with or without F-ara-A (5 µM), chlorambucil (20 µM), CAL-101 (1 µM), or rituximab (10 µg/ml). LC3 (red) shows autophagosomes, Lamp2 (green) shows lysosomes, DAPI (blue) shows nuclei. Images were collected with 60× objective and 4× optical zoom.

FIG. 2B: Quantification of LC3 fluorescence in CLL cells from FIG. 2A (n=6). LC3 fluorescence increases for F-ara-A and CAL-101 treatments were significant; P<0.0001).

FIG. 2C: Confocal fluorescence microscopy of CLL cells treated 4 hours with agent alone vs. agent+chloroquine (CQ, 0.5 µM).

FIG. 2D: Quantification of correlation index for LC3 and Lamp2 in CLL cells (n=5) treated with rapamycin (5 µM), CAL-101 (1 µM), thapsigargin (1 µM), F-ara-A (5 µM), with or without CQ (0.5 µM). Correlations of LC3 and Lamp2 were significant; rapamycin P=0.0004, thapsigargin P=0.0012, CAL-101 P=0.0002, F-ara-A P=0.0001.

FIG. 2E: Viability at 24 hours and 48 hours, shown as percent of annexin (ann) negative and propidium iodide (PI) negative cells (n=8) by flow cytometry. Cytotoxicity of thapsigargin was significantly enhanced by CQ addition (P=0.0008).

FIG. 2F: Viability at 24 hours in CLL cells (n=5) untransfected or transfected with scrambled siRNA or ATG5/7 siRNA and treated with F-ara-A (5 µM) or thapsigargin (1 µM). Thapsigargin cytotoxicity significantly increased in ATG5/7 siRNA samples (P=0.0047).

FIG. 3A: Confocal fluorescence microscopy for CLL cells untreated or treated 4 hours with flavopiridol (2 µM) or flavopiridol+CQ (0.5 µM). Samples were visualized as in previous figures.

FIG. 3B: Quantification of LC3 immunofluorescence in CLL cells from FIG. 3A. LC3 fluorescence was increased by flavopiridol and further by the addition of CQ (P<0.0001 for the increase with flavopiridol vs vehicle, the increase with flavopiridol+CQ vs vehicle, and the increase of flavopiridol+CQ vs flavopiridol).

FIG. 3C: Quantification of LC3-Lamp2 co-localization by average correlation index in 6 CLL samples treated with flavopiridol or flavopiridol+CQ as in FIG. 3A. The decreased co-localization with CQ was significant (P<0.0001).

FIG. 3D: Immunoblot for LC3B I and II and p62, representative of 3 experiments.

FIG. 3E: Quantification of LC3 immunofluorescence in a time course with flavopiridol. Following incubations, CLL cells (n=3) were collected by cytospin at the specified time points. Samples collected after the 4 hour time point were washed and resuspended in media without flavopiridol for the remainder of the incubation. The increase in LC3 fluorescence flavopiridol vs vehicle was significant (P=0.001) at 3, 4 and 8 hours, and decreased to levels comparable to vehicle alone at 12 and 24 hours.

FIG. 3F: Confocal fluorescence microscopy of CLL cells obtained from patients treated with flavopiridol in clinic. Samples were collected pre-treatment and at the end of flavopiridol infusion (4.5 hours) and visualized as in previous figures.

FIG. 3G: Average of LC3 fluorescence in CLL cells (n=16) collected from patients treated with flavopiridol in clinic, showing LC3 intensity at before treatment (PRE) and at the end of flavopiridol infusion (4.5 h). Overall, LC3 intensity was 1.44 times higher in non-responders compared to responders (95% CI: 1.07, 1.95; P=0.0183). Although the increase in intensity 4.5 hours vs. pre-treatment was slightly higher for non-responders compared to responders (fold change of 2.51 vs. 1.82), it was not significantly higher (P=0.3445).

FIG. 3H: Immunoblot for p62 in samples from CLL patients treated with flavopiridol. Samples were collected before treatment, at the end of flavopiridol infusion (4.5 hours) and at 24 hours from beginning of infusion. Data shown are representative of samples from 8 patients.

FIG. 4A: Viability of CLL cells (n=15) treated with flavopiridol and CQ. Live cells are shown by percent of annexin negative and PI negative cells at 24 hours. Cells were incubated with flavopiridol 4 hours; CQ was left on cells for 24 hours continuously. Viability decreased more with flavopiridol+CQ vs. flavopiridol alone (P=0.001).

FIG. 4B: Viability in CLL samples (n=10) untransfected or transfected with scrambled or combination ATG5/7 siRNA, then treated with flavopiridol (2 µM) for 4 hours. Treatments began 24 hours post-transfection. Percent of cells negative for annexin and PI was measured 24 hours from flavopiridol treatment (48 hours post-transfection). In flavopiridol-treated cells, viability was significantly lower in the presence of combination ATG5/7 siRNA vs. the scrambled control (P=0.004).

FIG. 6A: Confocal fluorescence microscopy for ATF6. Z stacks were collected (0.4 µm per slice) and images were chosen from the middle of nuclei. Side views (across bottom and side of figures) are also shown to depict ATF6 nuclear localization in CLL cells treated with flavopiridol (2 µM) or thapsigargin (1 µM) for 4 hours. Results shown are representative of 4 experiments.

FIG. 6B: ChIP assay data showing enrichment of ATF6 at the GRP78 promoter region with flavopiridol and thapsigargin treatment in 697 cells. Values of enrichment at promoter are presented relative to the IgG negative control.

FIG. 6C: ChIP assay data showing enrichment of ATF6 at GRP78 promoter region in cells from CLL patients undergoing flavopiridol treatment, collected before or at the end of flavopiridol infusion (4.5 hours).

FIGS. 6D-6E: Co-immunoprecipitation assay for IRE1-ASK1-TRAF2 complex formation. 697 cells (FIG. 6D) or samples from flavopiridol-treated CLL patients (FIG. 6E) were immunoprecipitated with TRAF2 and immunoblotted for ASK1 or IRE1.

FIG. 6F: Immunoblots for total and phosphorylated JNK1 and p38MAPK in CLL cells treated in vitro with flavopiridol (2 µM), thapsigargin (1 µM), F-ara-A (5 µM), rapamycin (5 µM). Results shown are from 2 representative patient samples.

FIG. 6G: Immunoblots for total and phosphorylated JNK1 and p38MAPK in samples from 6 CLL patients treated with flavopiridol in the clinic.

FIG. 11A: CLL cells (n=5) were transfected with scrambled or CDK-specific siRNA, and expression level of CDK5 was assessed by real-time RT-PCR. ACT was calculated by subtracting CT values for CD52 (our housekeeping gene) from CT values for CDK5. Higher values indicate lower gene expression.

FIG. 11B: Immunoblot for CDK1 and CDK5 in CLL cells incubated with different agents or transfected with CDK siRNA. CDK1 protein expression was undetectable in all CLL samples; lysate from Jurkat cells was used as positive control for the antibody.

FIG. 11C: Confocal fluorescence microscopy shows increased LC3 fluorescence in the presence of CDK5 siRNA compared to the scrambled control siRNA. Results shown are representative of 5 experiments FIG. 12D: Real-time RT-PCR CLL cells (n=5) transfected with CDK5 siRNA for XBP1. FIG. 12E: Real-time RT-PCR CLL cells (n=5) transfected with CDK5 siRNA for IRE1. FIG. 12F: Real-time RT-PCR CLL cells (n=5) transfected with CDK5 siRNA for GRP78.

FIG. 13A: Immunoblot for phosphorylation of eIF2α in the Jurkat cell line and CLL patient cells.

FIG. 13B: XBP1 splicing in cell lines, CLL cells and normal B cells. cDNA from various cells was subjected to XBP1-specific PCR, and products were separated on a 10% acrylamide gel. XBP1 splicing is detected with flavopiridol and thapsigargin in the cell lines 293T, RAW and 697, as well as in normal B cells, but was not detectable in CLL cells.

FIG. 14A: Activity of caspases 4 and 8 was measured in CLL cells obtained from patients before treatment, at the end of flavopiridol infusion (4.5 hours) and 24 hours after the beginning of the infusion.

FIG. 14B: real-time RT-PCR for ASK1 expression in CLL cells (n=5) transfected with scrambled or ASK1 siRNA, then incubated 4 hours with flavopiridol 2 µM, F-ara-A 5 µM, thapsigargin 1 µM, or tunicamycin 3 µg/ml (treatments were done 48 hours post-transfection). ACT was calculated by subtracting CT values for CD52 (our housekeeping gene) from CT values for ASK1. Higher values indicate lower gene expression.

FIG. 14C: Immunoblot for ASK1 after siRNA transfection. Lysates were collected after 4 hours incubation of cells with reagents described in FIG. 14B.

DETAILED DESCRIPTION OF THE PREFERRED EMBODIMENT(S)

Figure 1A:
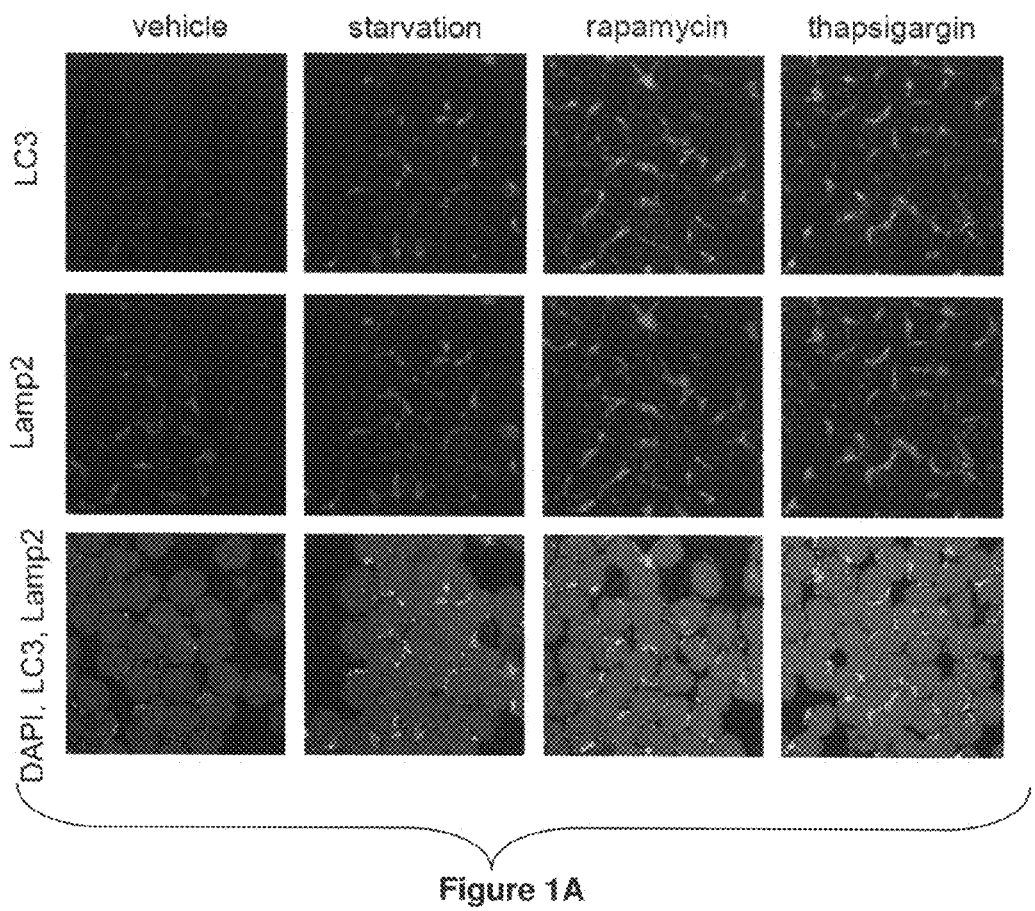
FIGS. 1A-1C: Autophagy in CLL cells.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Unless otherwise defined, all technical and scientific terms used herein have the same meaning as commonly understood by one of ordinary skill in the art to which these embodiments pertain. Although methods and materials similar or equivalent to those described herein can be used in the practice or testing of various embodiments, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The section headings used herein are for organizational purposes only and are not to be construed as limiting the described subject matter in any way. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

It is to be noted that the singular forms "a," "an," and "the" as used herein include "at least one" and "one or more" unless stated otherwise. Thus, for example, reference to "a pharmacologically acceptable carrier" includes mixtures of two or more carriers as well as a single carrier, and the like.

Numerous values and ranges are recited in connection with various embodiments of the present invention, e.g., amount of a compound or a therapeutic agent present in a composition. It is to be understood that all values and ranges which fall between the values and ranges listed are intended to be encompassed by the present invention unless explicitly stated otherwise. The term "about" as used herein in association with parameters, ranges and amounts, means that the parameter or amount is within ±0.1% of the stated parameter or amount.

The term "autophagy" refers to the catabolic process involving the degradation of a cell's own components; such as, long lived proteins, protein aggregates, cellular organelles, cell membranes, organelle membranes, and other cellular components.

The mechanism of autophagy may include: (i) the formation of a membrane around a targeted region of the cell, separating the contents from the rest of the cytoplasm, (ii) the fusion of the resultant vesicle with a lysosome and the subsequent degradation of the vesicle contents. For example, autophagy may inhibit the progression of some diseases and play a protective role against infection by intracellular pathogens.

The term "autophagy modulating compound" refers to a compound that induces autophagy in a cell. The term autophagy modulating compound, as used herein, comprises the specific compounds disclosed herein.

The term "autophagy associated disease" includes a disease that can be treated by the induction of autophagy. Examples of such diseases include diseases caused by misfolded protein aggregates. The term "disease caused by misfolded protein aggregates" is intended to include any disease, disorder or condition associated with or caused by misfolded protein aggregates. The term "autophagy associated disease" also includes cancer; for example, any cancer wherein the induction of autophagy would inhibit cell growth and division, reduce mutagenesis, or kill developing tumor cells. Also, "autophagy associated diseases can be chronic diseases, including lymphoproliferative diseases.

The term "chronic disease" refers to a persistent and lasting disease or medical condition, or one that has developed slowly.

The term "effective" amount refers to the amount of an autophagy modulating compound of the present invention required to treat or prevent an autophagy associated disease. The effective amount of an autophagy modulating compound of the invention used to practice the invention for therapeutic or prophylactic treatment of autophagy associated diseases varies depending upon the manner of administration, the age, body weight, and general health of the subject. An effective amount of an autophagy modulating compound, as defined herein may vary according to factors such as the disease state, age, and weight of the subject, and the ability of the autophagy modulating compound to elicit a desired response in the subject. Dosage regimens may be adjusted to provide the optimum therapeutic response. Non-limiting examples include: an effective amount is also one in which any toxic or detrimental effects (e.g., side effects) of the autophagy modulating compound are outweighed by the therapeutically beneficial effects. A therapeutically effective amount of an autophagy modulating compound (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an autophagy modulating compound can include a single treatment or, preferably, can include a series of treatments. In one example, a subject is treated with an autophagy modulating compound in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of an autophagy modulating compound used for treatment may increase or decrease over the course of a particular treatment.

The terms "pharmaceutical composition" and/or "therapeutic agent" and/or "agent" refer to a compositions formulated with one or more pharmaceutical-grade excipients in a manner that conforms with the requirements of a governmental agency regulating the manufacture and sale of pharmaceuticals as part of a therapeutic regimen for the treatment or prevention of disease in a mammal (e.g., manufactured according to GMP regulations and suitable for administration to a human). Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

The term "pharmaceutically acceptable carrier" refers to any such carriers known to those skilled in the art to be suitable for the particular mode of administration. For example, the term "pharmaceutically acceptable carrier" includes any and all solvents, dispersion media, coatings, antibacterial and antifungal agents, isotonic and absorption delaying agents and the like, that may be used as a media for a pharmaceutically acceptable substance. In addition, the active materials can also be mixed with other active materials that do not impair the desired action, or with materials that supplement the desired action, or have another action.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

The term "subject" includes humans, and non-human animals amenable to therapy, including mammals and animals susceptible to an autophagy associated disease, including non-human primates, transgenic animals, mice, rats, dogs, cats, rabbits, pigs, chickens, sheep, horses, and cows. Preferably, the subject is a human subject.

In one aspect, the present invention provides a method for inducing autophagy that may serve as the basis for new therapies.

In another aspect, the present invention provides compounds, compositions and combination therapies that are useful as autophagy modulating agents It is also to be understood that the present invention includes methods for screening, selecting, and discovering compounds that are useful as agents for modulating autophagy.

The present invention also provides autophagy-based treatment methods for treating diseases.

Embodiments according to this aspect of the present invention generally include the steps of: administering a pharmaceutically effective amount of a pharmaceutical composition according to the described aspects and other contemplated aspects of the present invention.

In another aspect, the present invention relates to compositions and methods for augmenting the therapeutic activity of anticancer agents. In particular, this activity is augmented by sensitizing cancer or tumor cells through modulation of the Endoplasmic Reticulum (ER) stress response pathway.

Embodiments

The present invention is based, at least in part, on the inventors' discovery, while studying the mechanisms of action of flavopiridol in chronic lymphocytic leukemia (CLL), that flavopiridol induces autophagy in CLL cells in vitro and in vivo.

While precise knowledge of the mechanism of the synergism due to the combination is not necessary to the practice of the invention, a brief discussion of the putative mechanism may be helpful to understanding of the invention. Of course, because precise knowledge of the mechanism is not necessary to the practice of the invention, the inventors expressly do not wish to be bound to any discussion of mechanism present herein.

Autophagy is an intracellular process that plays a role in the normal cell homeostasis by mediating the normal turnover of long-lived proteins and intra-cellular organelles. Autophagy can play an essential role in cell survival under nutrient restriction conditions and is an essential process in development. In addition, autophagy can antagonize cell survival and promote cell death—type II, autophagic cell death—when "the point of no return" is crossed by overstimulation of autophagy, leading to disintegration of essential cellular components.

The process of autophagy involves the sequestration of misfolded proteins, damaged/aged organelles or other intracellular components inside a double membrane vesicle called "autophagosome" which subsequently fuses with a lysosome and all contents are degraded by lysosomal enzymes.

There are more than 31 autophagy-related proteins (ATGs) genes that have been identified and linked to autophagy regulation. Among them, ATG8, better known by the human homolog name LC3, represents the most specific marker of autophagy. LC3 is a cytoplasmic protein which upon autophagy induction is conjugated with phosphatydilethanolamine and recruited to the autophagosome membrane, contributing to its formation and expansion. Autophagosome formation is mediated also by the class III phosphatidylinositol 3-kinase (class III PI3K) which forms a complex with Beclin-1 (ATG6) and Barkor (Beclin 1—associated autophagy related key regulator, homolog of ATG14).

The inventors herein investigated the cytoplasmic LC3 protein in CLL cells treated with flavopiridol in vitro, and found a significant increase in the protein expression, detected by western blot and confocal immunofluorescence. The increase of LC3 in the cells treated with Flavopiridol was comparable to the increase seen with rapamycin (mammalian target of rapamycin).

Moreover, an increase in LC3 was detected also in CLL cells selected from patients who received flavopiridol treatment in clinic. The samples collected at 4 hours after starting the flavopiridol infusion showed a significant accumulation of autophagosomes in comparison to the samples collected before the treatment and at 24 hours after treatment. The patients who did not respond to flavopiridol therapy had a higher increase in LC3 in comparison to the patients who responded to the therapy. This shows that flavopiridol is able to induce autophagy both in vitro and in vivo and it also shows that autophagy may be a mechanism of resistance to flavopiridol.

In view of these discoveries, the inventors then determined whether autophagy in this context is a mechanism for cell death or cell survival, and whether an accumulation of the autophagosomes is due to a real induction of autophagy or rather due to the blockage of autophagosomes degradation. To make such determination, the inventors tested the effect of chloroquine, a classical anti-malarial drug that has the ability to inhibit autophagy by preventing fusion of autophagosomes with lysosomes and subsequent degradation of their cargo by the lysosomal enzymes.

Treatment in vitro of CLL cells with a combination of chloroquine and flavopiridol or ATG5/ATG7 siRNA and flavopiridol-enhanced the cytotoxicity relative to flavopiridol alone, as detected by measuring viability with Annexin/PI staining using flow cytometry. In addition, the inventors observed an increase in LC3 in the presence of combination of flavopiridol and chloroquine, versus flavopiridol alone—indicating that the accumulation of autophagosomes seen in the flavopiridol treated samples is caused by stimulation of autophagy and not by inhibition of autophagosome degradation.

Among the mechanisms of autophagy induction, one is that increases in free cytosolic calcium can stimulate macroautophagy. One of the main sources of intracellular calcium is endoplasmic reticulum. Endoplasmic reticulum stress has also been implicated in the induction of autophagy.

The inventors' results show an increase of intracellular calcium in CLL cells treated with flavopiridol accompanied by an increased expression of genes involved in endoplasmic reticulum stress response (XBP1, IRE1, GRP78, BIP). These findings show that the endoplasmic reticulum may be the primary target of flavopiridol, and the stress of this organelle potentially triggering the cascade of events leading to stimulation of autophagy as a strategy of cells to survive to this treatment.

The examples herein further demonstrate that the autophagy induced by flavopiridol in CLL cells is a cell survival signal and that autophagy contributes to the drug resistance which is usually observed in approximately 40% of the CLL patients treated with this drug. This process is an attractive target for combinational therapies that can enhance Flavopiridol efficacy by overcoming the resistance conferred by stimulation of autophagy.

EXAMPLES

The following examples are included to demonstrate embodiments. It should be appreciated by those skilled in the art that the techniques disclosed in the examples which follow represent techniques discovered by the inventors to function well in practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

Example 1

Example 1 demonstrates that autophagy induced by ER stress, but not other mechanisms, protects CLL cells from cell death and that the CDK inhibitor flavopiridol robustly induces both ER stress and a protective autophagic response.

Described herein is a detailed study of endoplasmic reticulum (ER) stress now showing the mechanism of CDK inhibitor-mediated cell death. These studies demonstrate for the first time that flavopiridol induces robust ER stress in vitro and in patients, and that subsequent cell death is dependent upon IRE1-induced ASK1 activation and downstream caspase 4. Use of this mechanism of action of flavopiridol and other CDK inhibitors now provides a method for overcoming resistance to various CLL treatments now being currently used in treatments of CLL patients.

Results for Example 1

CLL Cells Express Autophagy-related Proteins and are Susceptible to Autophagy Induced by Starvation or Pharmacologic Agents:

Given the absence of reports on autophagy in CLL, the inventors herein first examined whether CLL cells express the critical components of this pathway. As shown in FIG. 7, autophagy pathway proteins including ATG family members, are clearly expressed in primary CLL cells at levels comparable to normal B cells. ATG4C, UVRAG and ULK1 were increased in CLL samples. The inventors next determined if CLL cells undergo autophagy with well-characterized initiators of this process. As depicted by confocal fluorescence microscopy in FIG. 1A and numerically quantified in FIG. 1B, CLL patient samples (n=6) undergoing 4 hours of starvation or 4 hours incubation with thapsigargin or rapamycin show significant (P<0.0001 treatment versus vehicle-treated for all conditions) increase in LC3 aggregation, indicating increased autophagosome formation. The anti-LC3 antibody used here to detect autophagosomes is the same as the one used next for the immunoblot experiment; it detects uncleaved LC3B, LC3-I and LC3-II. The LC3-II form is usually very bright due to the dotted pattern, completely overpowering the intensity of uncleaved and LC3-I forms, which are virtually comparable to the background due to the homogenous spread in the cell. Therefore, when we refer to LC3 fluorescence intensity, we are in fact presenting the LC3-II form, which localizes to the walls of the autophagosomes. Formation of autophagosomes was also confirmed by immunoblot (41) showing increased LC3-II (FIG. 1C). Autophagosome accumulation can be caused either by induction of their formation or by inhibition of fusion with lysosomes.

Figure 1B:
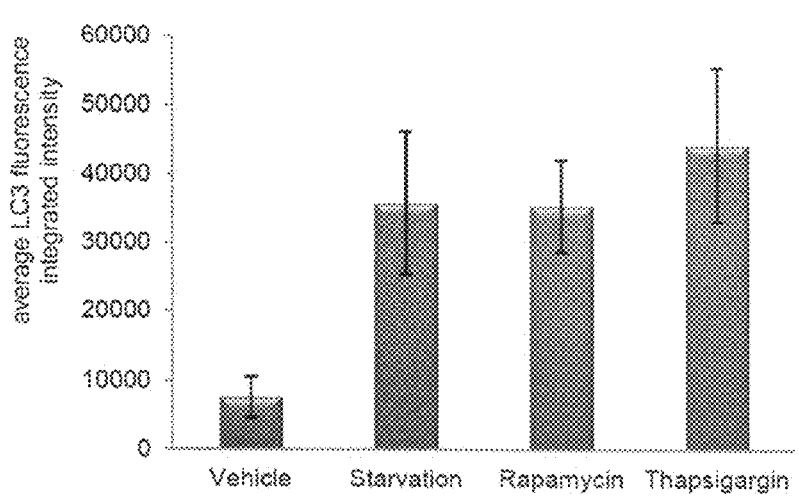
Figure 1C:
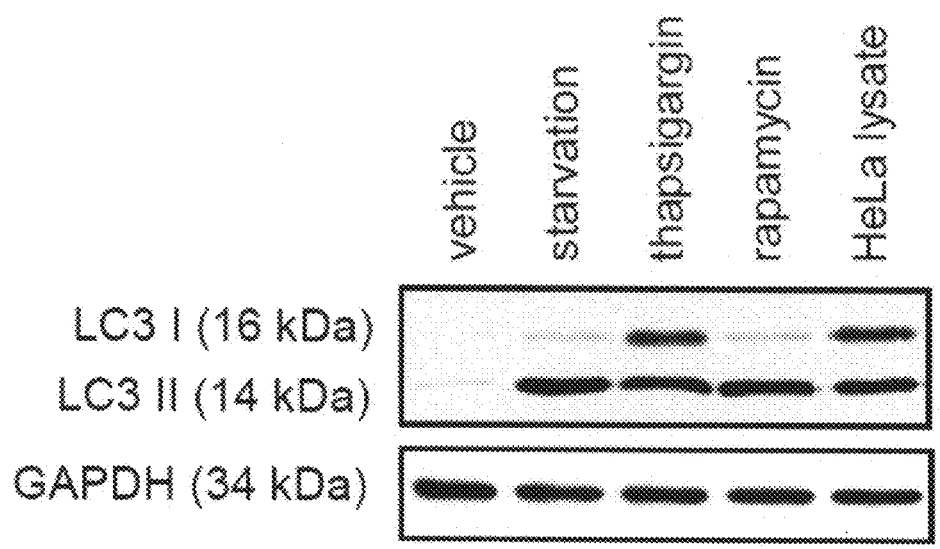

In FIG. 1A, autophagosome-lysosome fusion is demonstrated by co-localization of LC3 and the lysosome marker Lamp2, thereby showing full execution of autophagy flux. Collectively, these studies show that autophagy occurs in CLL cells following classic stimuli.

Figure 2A:
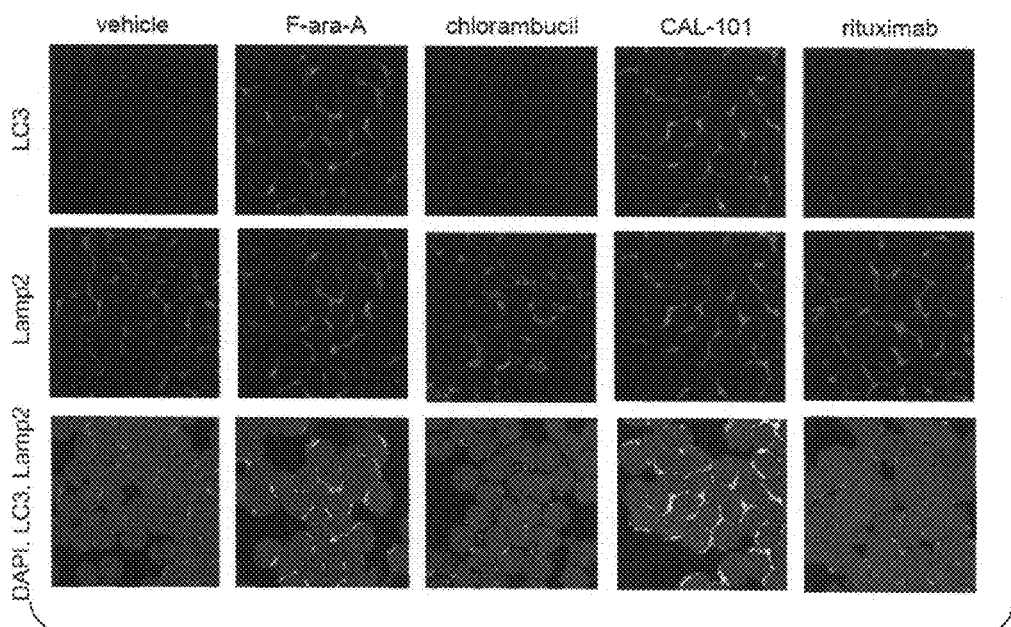
FIGS. 2A-2F: Specificity and role of autophagy in CLL cells.
Figure 2B:
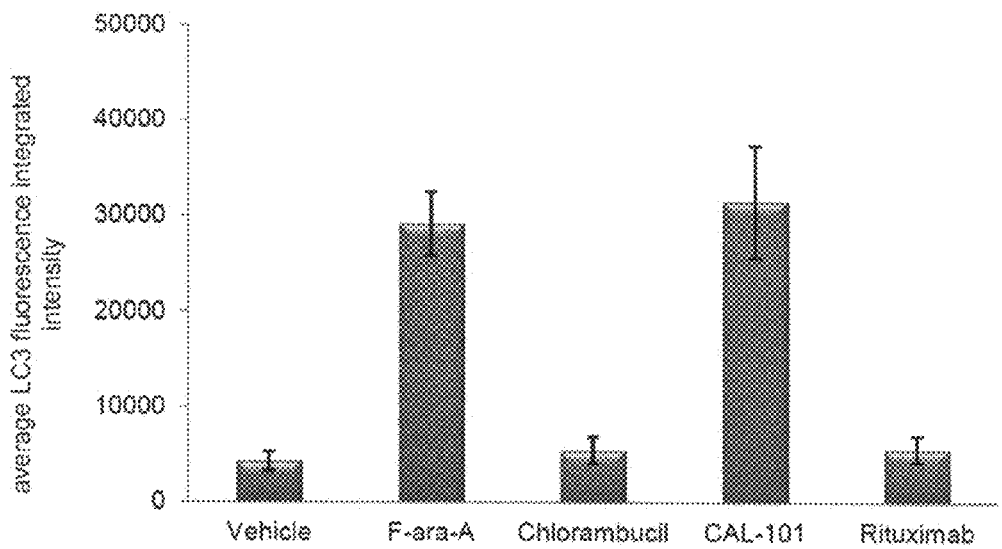
Figure 9:
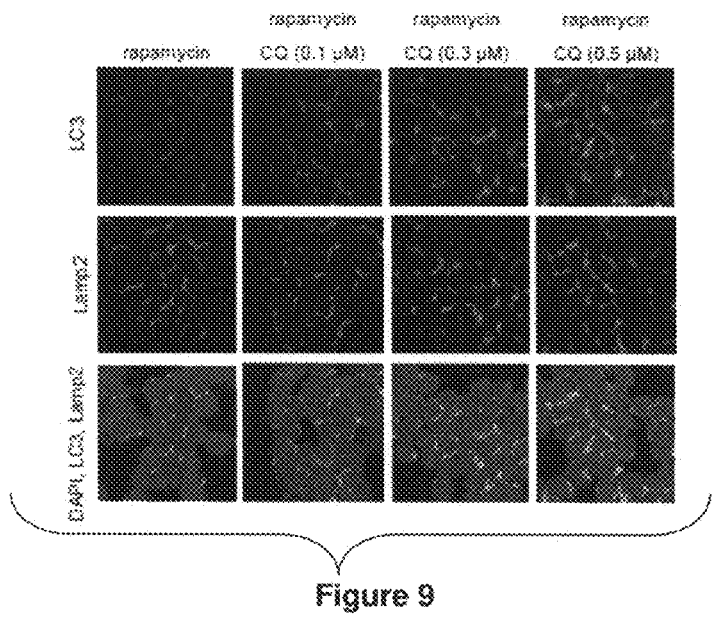
FIG. 9: Chloroquine inhibits LC3-Lamp2 co-localization. CLL cells were incubated with 5 µM rapamycin, with or without chloroquine at several concentrations. Confocal fluorescence microscopy shows LC3 (autophagosomes) in red, Lamp2 (lysosomes) in green and DAPI (nuclei) in blue. Images were collected with 60× objective and 4× optical zoom.

Inhibition of ER Stress-induced Autophagy, but not mTOR Inhibitor—, CAL-101—, or Fludarabine-induced Autophagy, Enhances CLL Cell Death:

In normal and cancer cells, autophagy promotes either survival or cell death, depending on context. The inventors determined whether autophagy protects CLL cells from death, using autophagy stimuli examined in FIG. 1 and also agents used to treat this disease. As shown in FIG. 2A and quantified in FIG. 2B, the inventors observed by confocal immunofluorescence microscopy a significant (P<0.0001; n=6) induction of autophagy with either the metabolically active form of fludarabine F-ara-A or the PI3K inhibitor CAL-101, as evidenced by autophagosome accumulation and subsequent fusion with lysosomes. In contrast, neither chlorambucil nor rituximab produced this effect. This shows that autophagy is not a uniform occurrence with all agents used in CLL. To investigate the impact of autophagy in either promoting or protecting CLL cells from death, the inventors utilized chloroquine (abbreviated as CQ in figure legends), an agent that prevents fusion of the autophagosome with the lysosome. In these experiments, chloroquine did in fact inhibit autophagosome-lysosome fusion at 0.1-0.5 µM, concentrations attainable in patients receiving this for malaria treatment (FIG. 9).

Figure 2C:
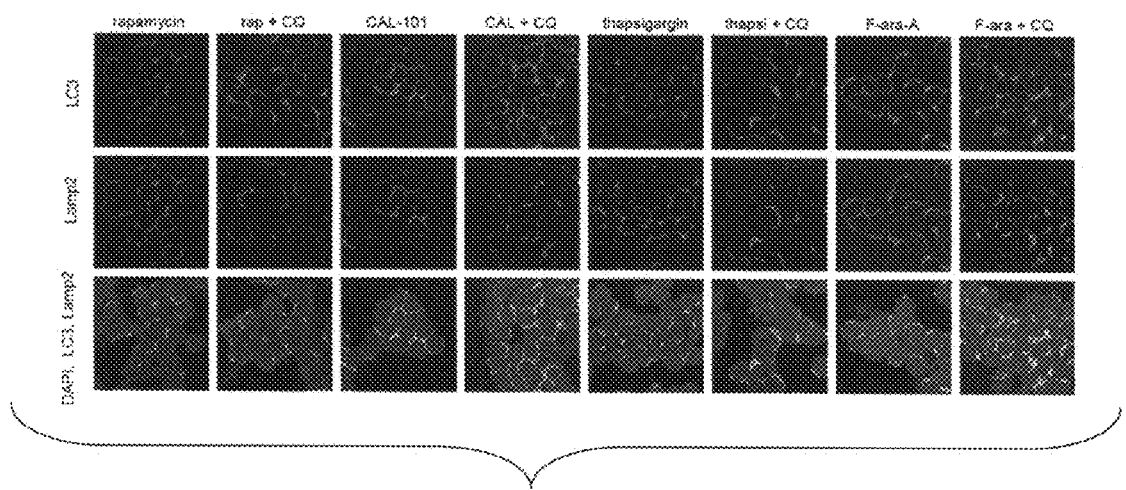
Figure 2D:
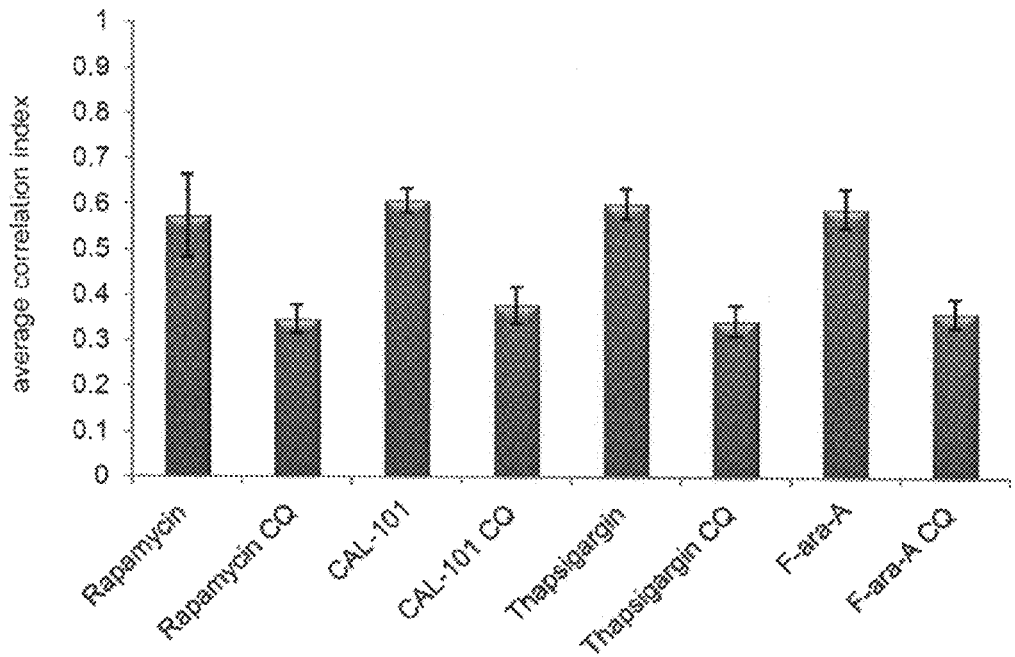

In FIGS. 2C and D, the inventors demonstrate by confocal microscopy and quantification of images that in CLL patient cells (n=6), the addition of chloroquine to rapamycin (P=0.0004), thapsigargin (P=0.0012), CAL-101 (P=0.0002) or fludarabine (P=0.0001) prevents fusion of autophagosomes with lysosomes at 4 hours compared to each agent alone. Quantification of co-localization was done by measuring the correlation index, which reflects the degree of overlap between red (LC3) and green (Lamp2) signals; if the index is 1, it indicates complete overlap, 0 is no overlap. Vehicle only and vehicle plus chloroquine conditions were not included in the quantification due to the fact that when autophagy is not stimulated, the signal for Lamp2 overpowers the signal for LC3 and co-localization between the two is not assessable.

Figure 2E:
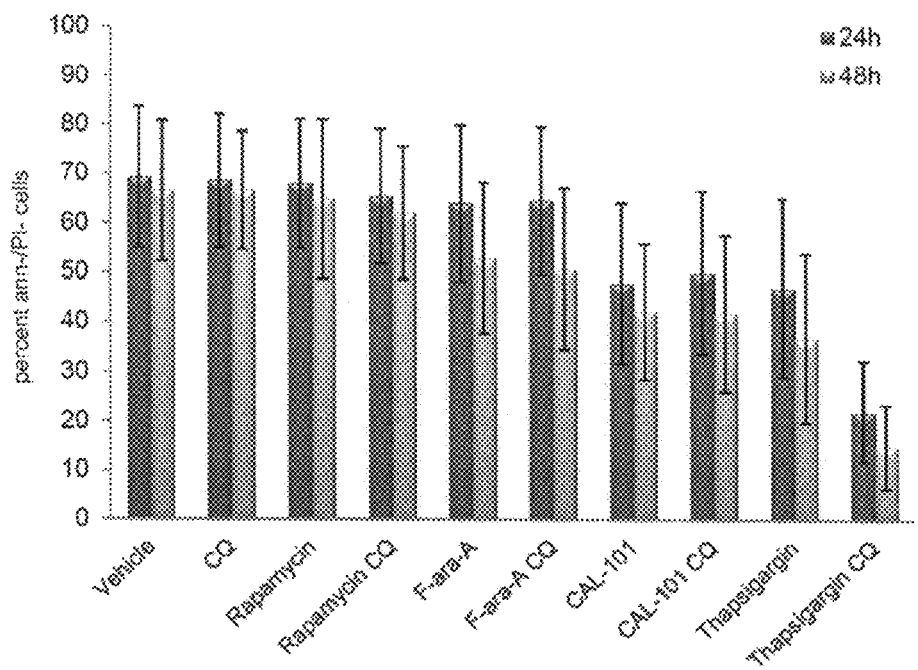

Interestingly, chloroquine neither enhanced nor diminished cell death promoted by rapamycin, CAL-101 or fludarabine, nor did it affect cell viability by itself. In contrast, cell death caused by the ER stress-inducing agent thapsigargin was significantly enhanced by the addition of chloroquine (P=0.0008) (FIG. 2E).

Figure 2F:
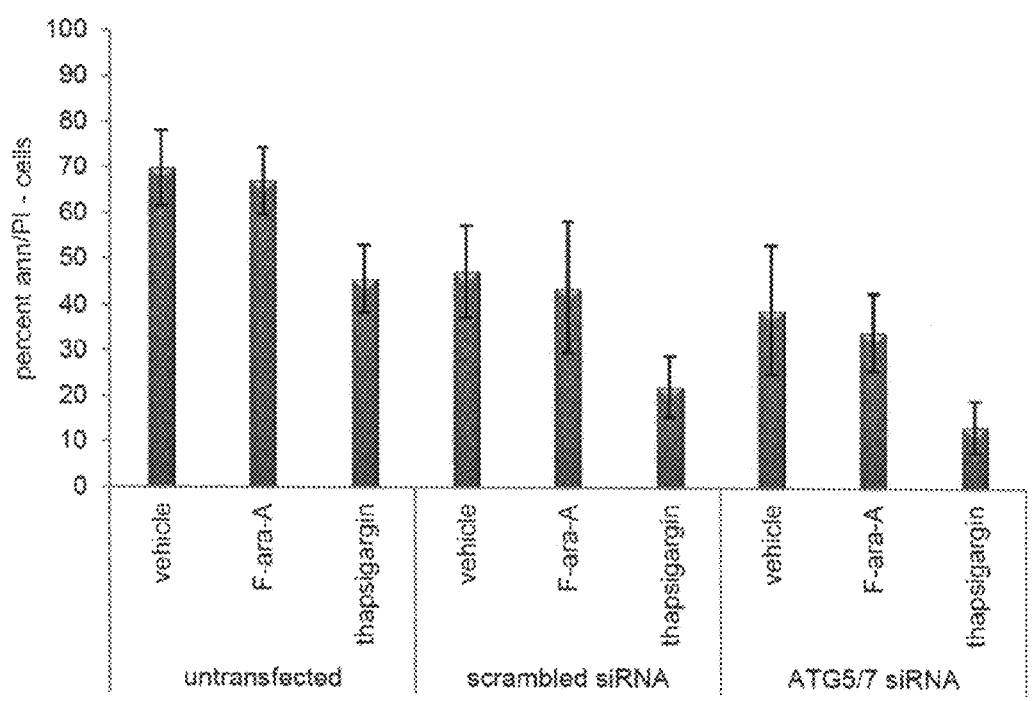
Figure 10A:
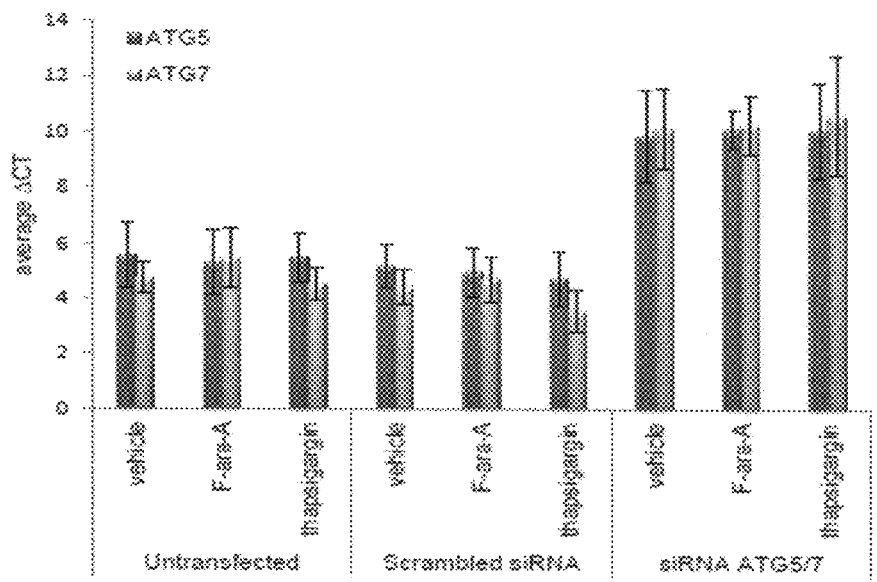
FIGS. 10A-10B: Expression of ATG5 and ATG7 with siRNA treatment. CLL cells were transfected with scrambled or combination of ATG5 and ATG7 siRNA. 24 hours after transfection, cells were incubated 4 hours without or with (FIG. 10A) thapsigargin (1 µM) or F-ara-A (5 µM), or (FIG. 10B) flavopiridol (2 µM). RNA was collected at the end of the treatment and analyzed by real-time RT-PCR. ATG5 and ATG7 expression was significantly reduced by siRNA (P<0.0001). For (FIG. 10A), n=5, for (FIG. 10B), n=10. ACT was calculated by subtracting CT values for CD52 (our housekeeping gene) from CT values for ATG5 and ATG7. Higher values indicate lower gene expression.

To confirm that the enhanced killing in the presence of chloroquine was not due to an off-target effect, siRNA directed at ATG5/ATG7 was used. As shown in FIG. 10A, ATG5/ATG7 expression in CLL cells was significantly reduced (P<0.0001) with ATG5/ATG7 siRNA. In these cells, cytotoxicity of thapsigargin was significantly (P=0.0047) enhanced compared to cells transfected with the scrambled siRNA control (FIG. 2F). Together, these studies show that autophagy induced with traditional stimuli and common CLL therapeutics does not serve as a mechanism of resistance in CLL cells. In contrast, ER stress-induced autophagy does antagonize death induced by thapsigargin and potentially other ER stress-inducing drugs.

Flavopiridol Promotes Autophagy In Vitro and In Vivo in CLL Cells

Figure 3A:
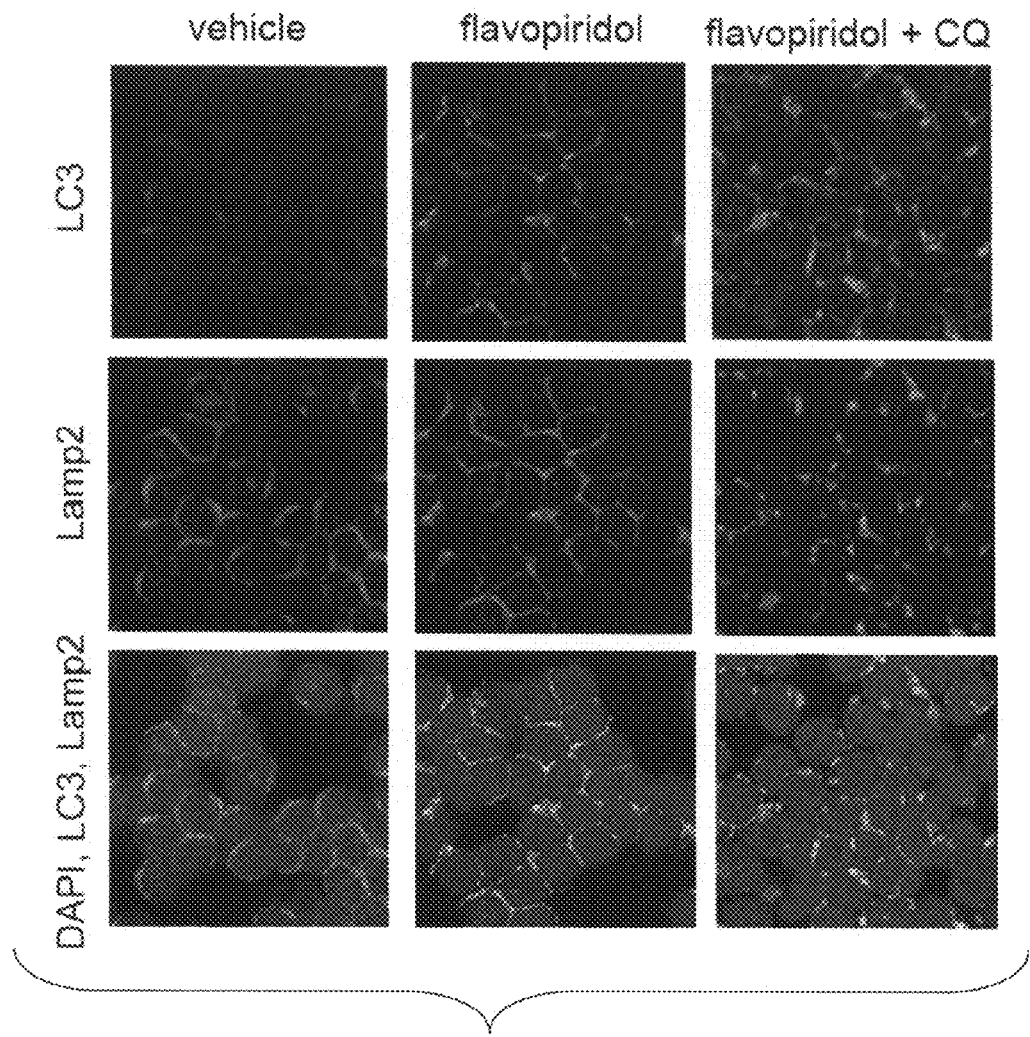
FIGS. 3A-3H: Autophagy in CLL cells treated with CDK inhibitor flavopiridol.
Figure 3B:
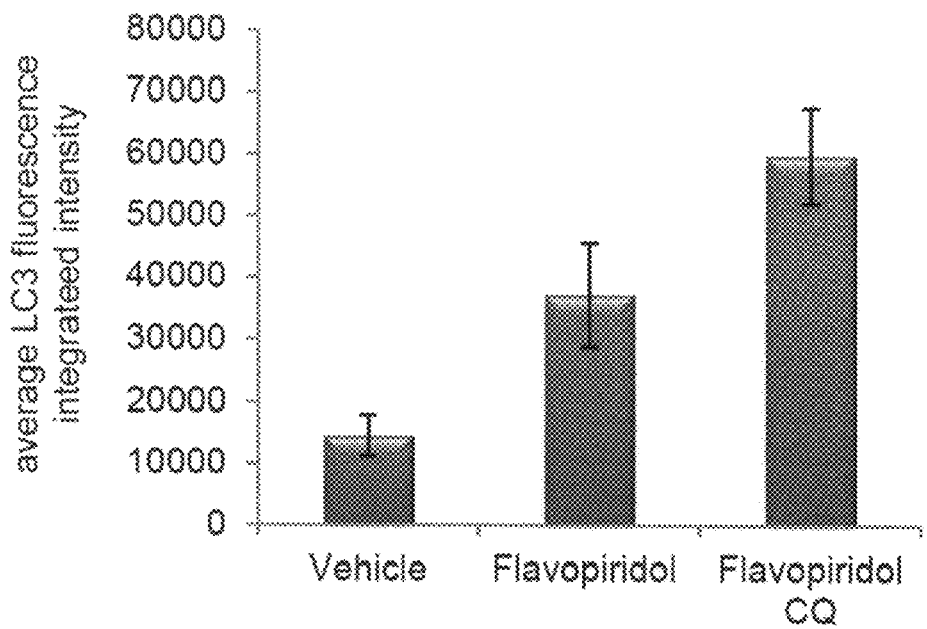
Figure 3C:
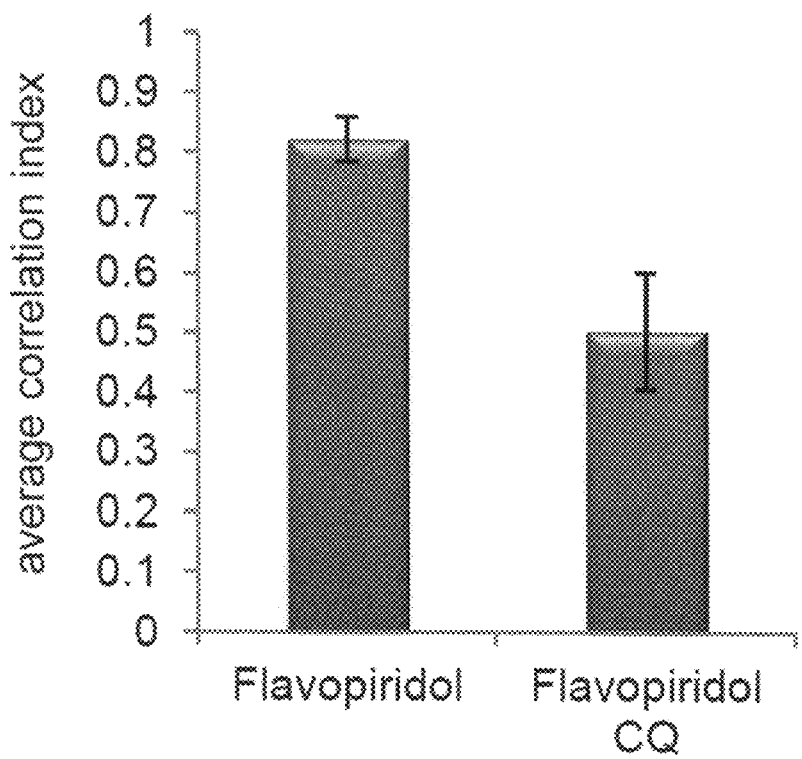
Figure 3D:
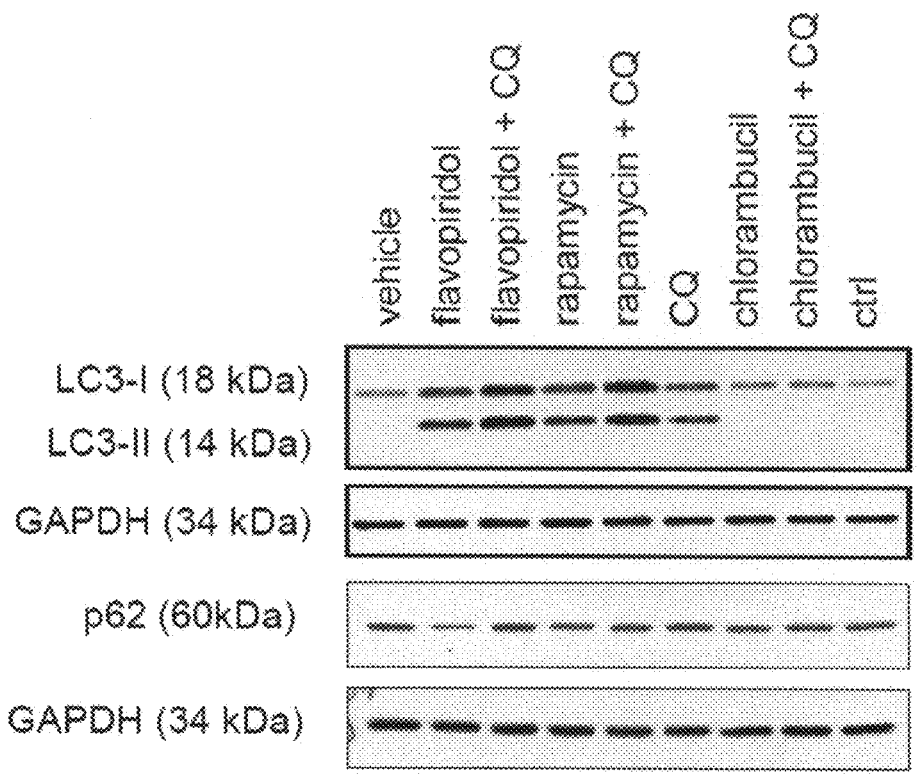
Figure 3E:
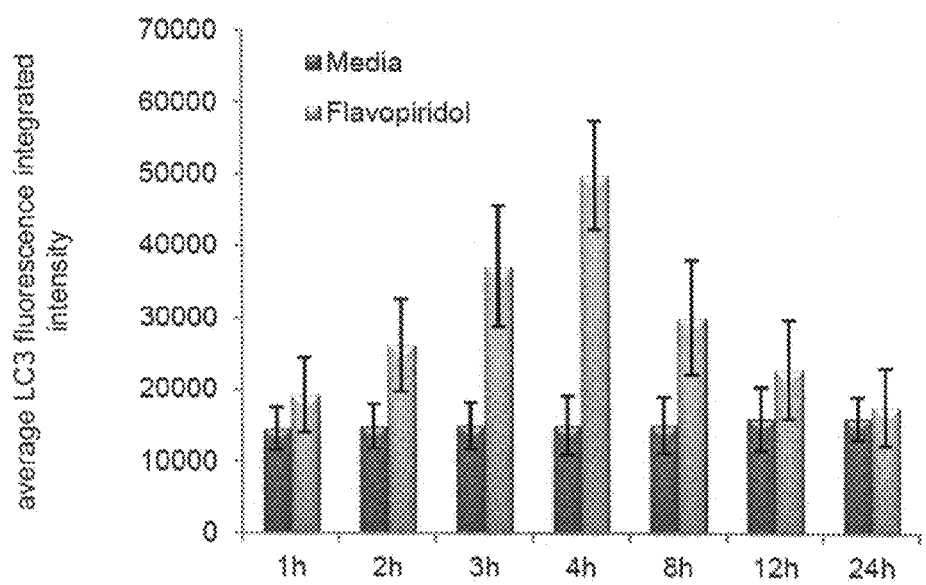

CLL cells (n=6) were incubated 4 hours with or without flavopiridol and examined by immunofluorescence microscopy. Significant (P=0.0001) formation of autophagosomes was observed in flavopiridol-treated cells compared to the vehicle control (FIGS. 3A and B). Concurrently, unrestricted autophagy flux was demonstrated by co-localization of LC3 and Lamp2 (quantified in FIG. 3C). Induction of autophagy in flavopiridol-treated cells was also shown by immunoblot for LC3 and signaling adaptor protein p62 (FIG. 3D). p62 is a target of the autophagic process, thus a decrease of this protein suggests induction of the autophagy flux. Consistent with this, p62 levels are decreased in the presence of flavopiridol. However, it has been shown that levels of p62 are not regulated exclusively by autophagy; therefore p62 cannot be taken as an absolute marker of autophagy flux. Autophagy flux was examined also in a time course with flavopiridol (FIG. 3E), which revealed a significant (P=0.0008) accumulation of autophagosomes (increased LC3 fluorescence intensity) until 4 hours of treatment, followed by a decrease in LC3 intensity after 8 hours of treatment, likely due to degradation of autophagosomes by the lysosomal enzymes.

Figure 11A:
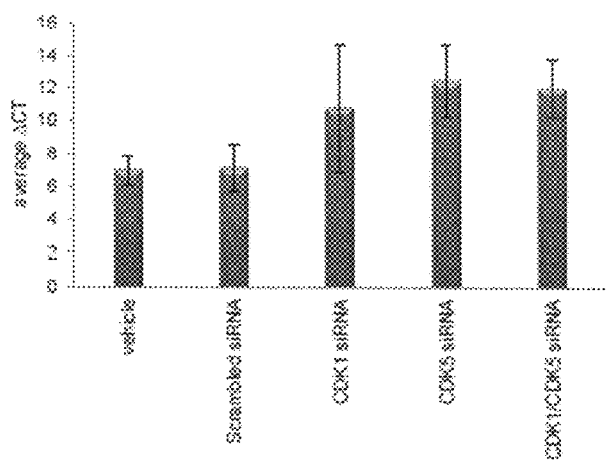
FIG. 11A-11C: Effects of CDK1 and CDK5 knockdown on autophagy.
Figure 11B:
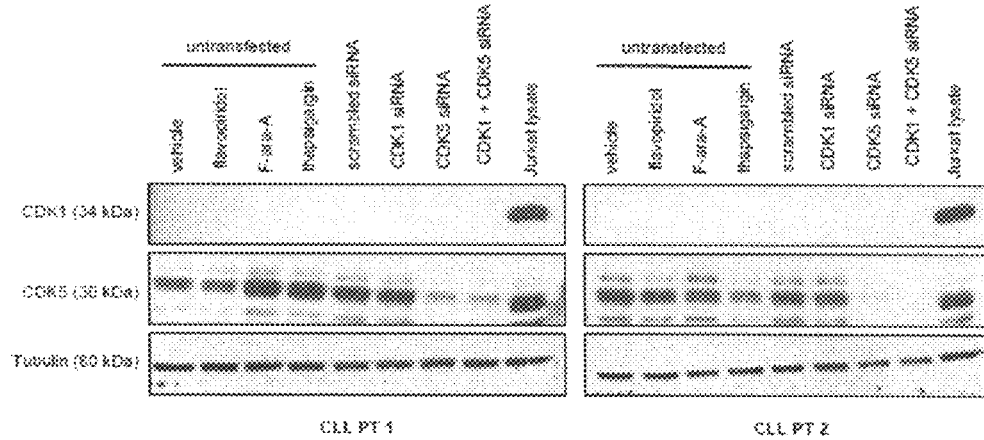
Figure 11C:
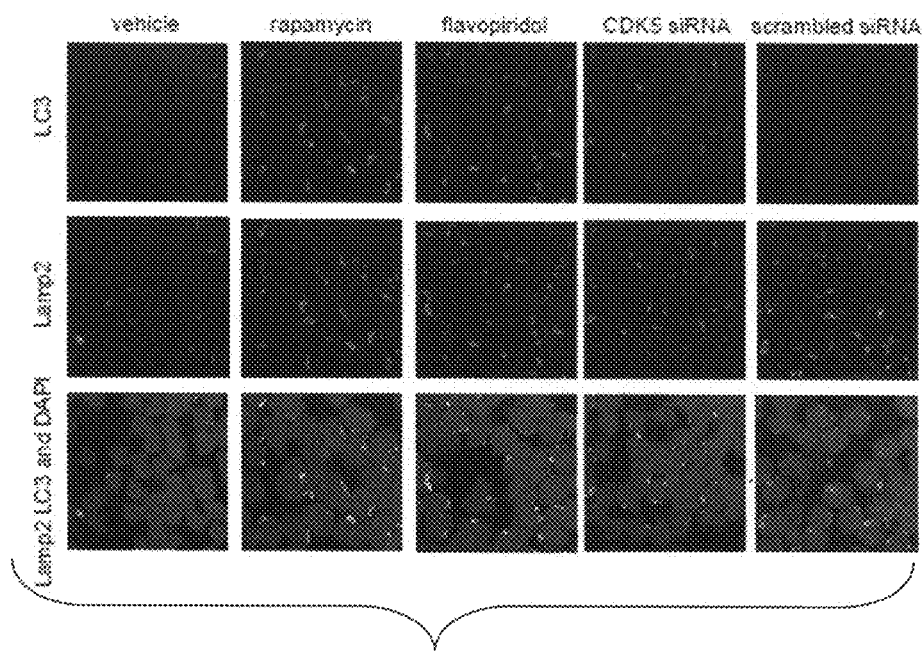

To determine if flavopiridol-mediated autophagy is due to inhibition of CDK versus an alternative kinase, we next examined CDK1 and CDK5, both targeted by flavopiridol and demonstrated to prevent autophagy initiation through phosphorylation of Vps34. As shown in FIG. 11A, CDK5 is expressed in CLL patient cells, whereas CDK1 was below the level of detection both by real-time RT-PCR ($C_T$ values ~32-34) and by immunoblot. Cells transfected with siRNA to CDK5 or combination of siRNA against CDK1 and CDK5 exhibited a decrease in CDK5 expression (FIGS. 11A, 11B) and an increase in autophagy (FIG. 11C) compared to cells transfected with scrambled siRNA, indicating that flavopiridol-induced autophagy in CLL cells is mediated at least in part via CDK5 inhibition.

Figure 3F:
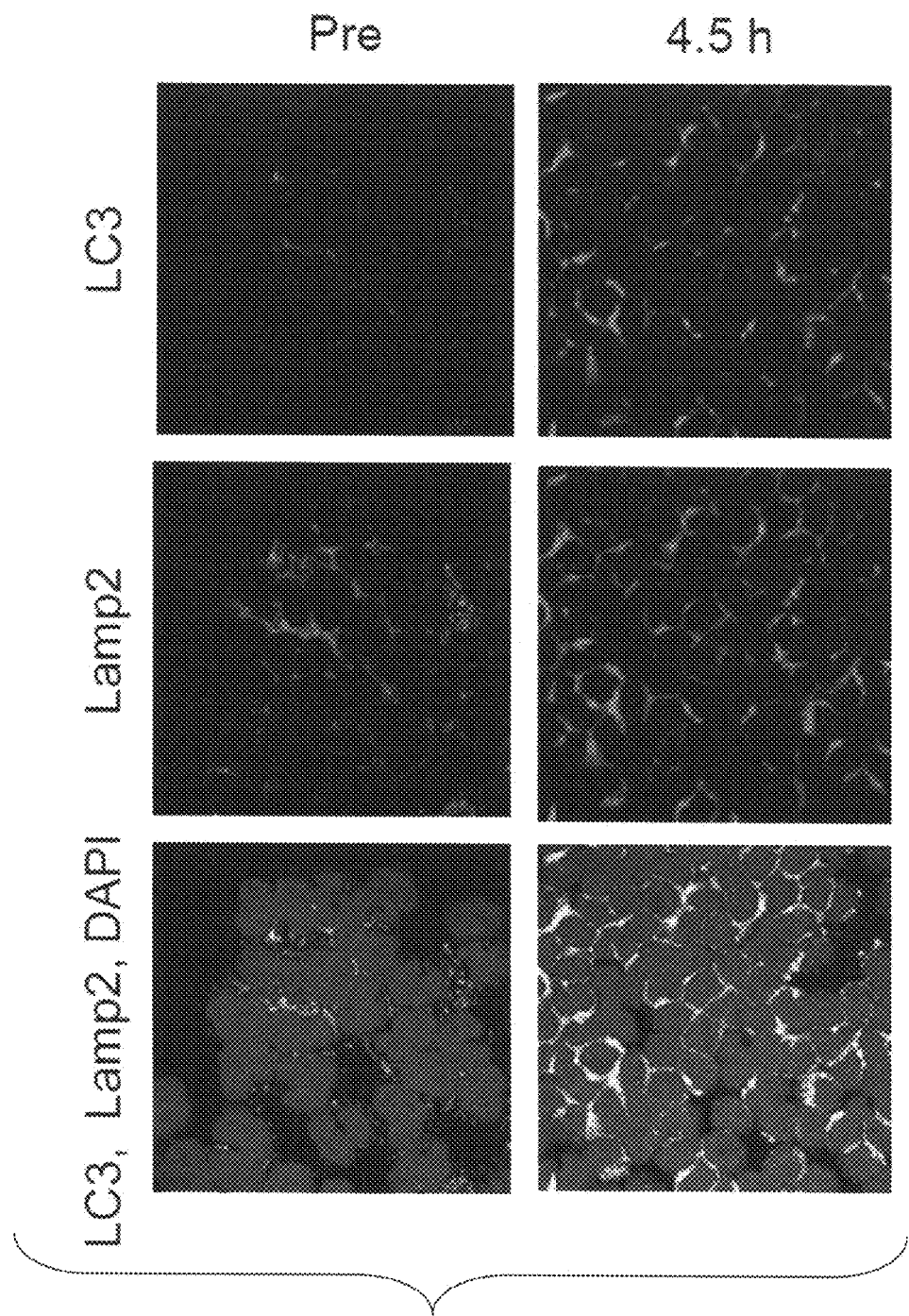
Figure 3G:
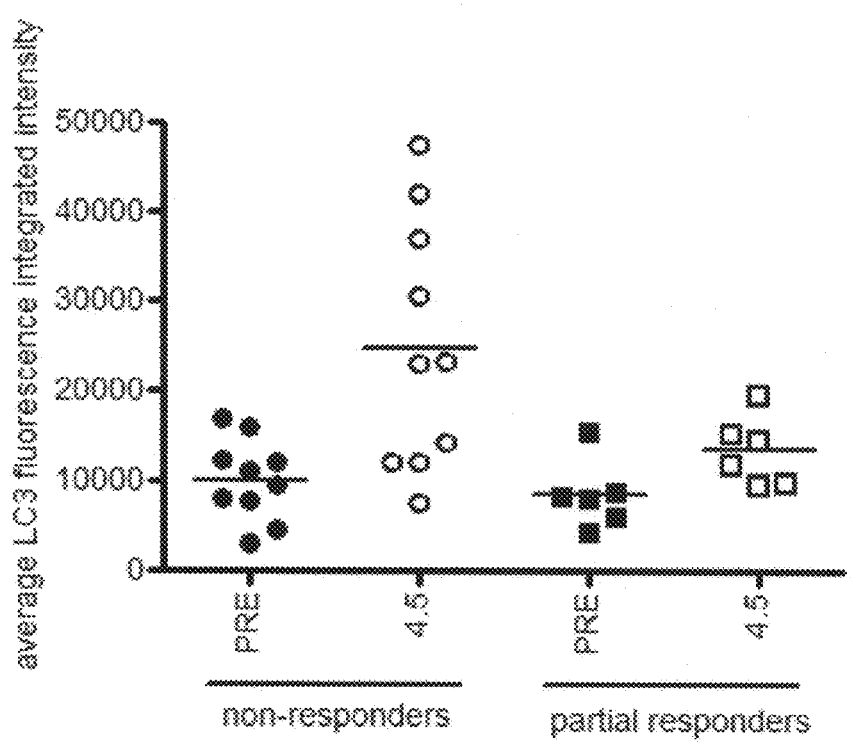
Figure 3H:
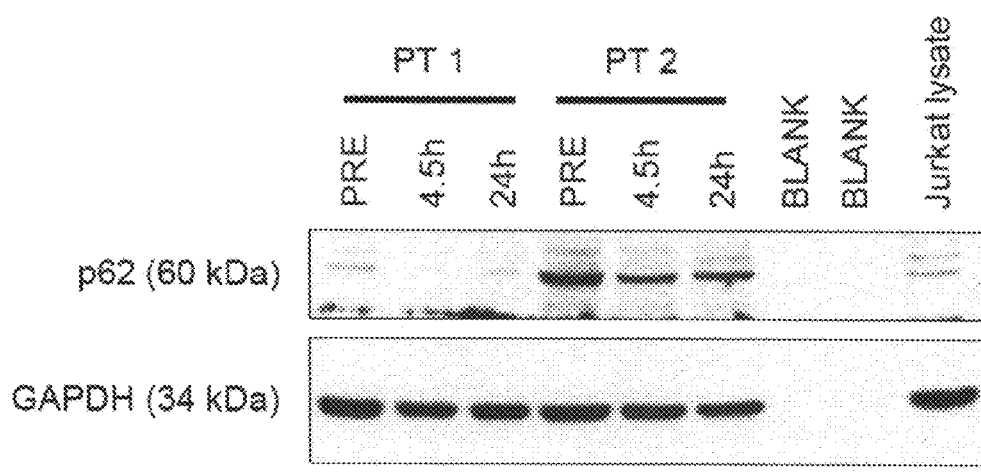

The inventors next determined whether induction of autophagy occurred in CLL patients treated with flavopiridol, using samples from patients enrolled on clinical trial OSU-0491 (NCI 7000; ClinicalTrials.gov NCT00098371), a phase II multicenter study of flavopiridol administered as 30 minute loading dose followed by four-hour continuous infusion in patients with previously treated CLL. In this trial, CLL cells were collected pre- and post-therapy 4.5 hours, day 1 (n=16). By confocal fluorescence microscopy, both increased autophagosome formation (P=0.0011) and fusion with lysosomes is observed (FIG. 3F). Analysis of LC3 integrated intensity showed that there was an average of 2.16 fold increase in fluorescence at 4.5 hours after flavopiridol infusion versus pretreatment (FIG. 3G). The level of autophagy, as assessed by LC3 fluorescence intensity, was overall greater in non-responders versus responders in both pre- and post-treatment samples (P=0.018); however, the increase in intensity at 4.5 hours post- vs. pre-treatment was only slightly higher for non-responders compared to responders (fold change of 2.51 vs. 1.82, P=0.3445). We also confirmed the increase in autophagy flux after flavopiridol therapy by p62 immunoblot, which shows a decrease in protein expression in samples collected at 4.5 hours post flavopiridol infusion (FIG. 3H). Collectively, these studies provide evidence that our in vitro observations are relevant to the clinical setting.

Figure 4A:
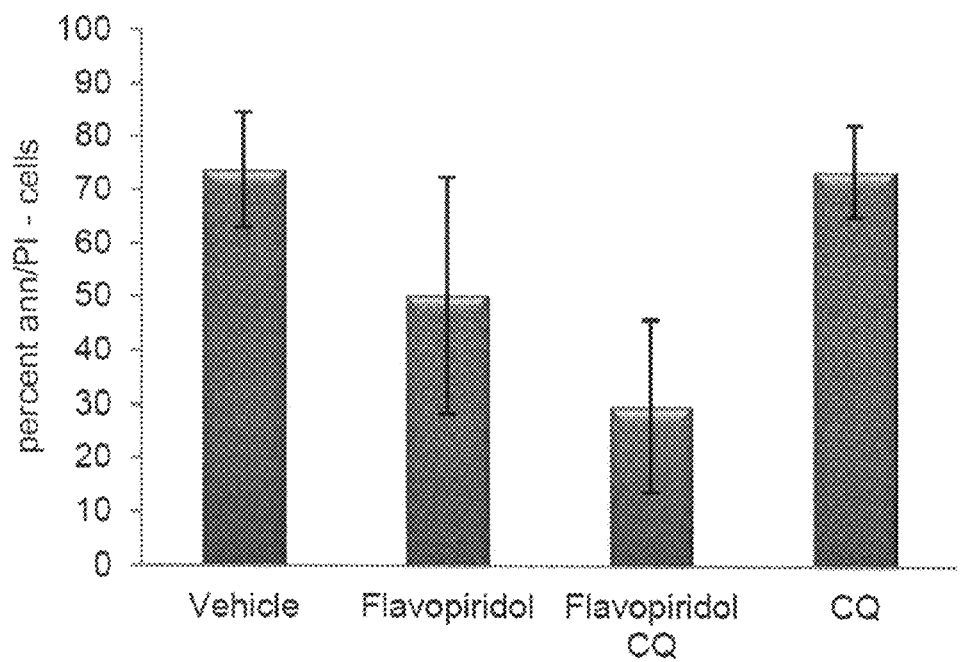
FIGS. 4A-4B: Inhibition of flavopiridol-induced autophagy in CLL cells.
Figure 4B:
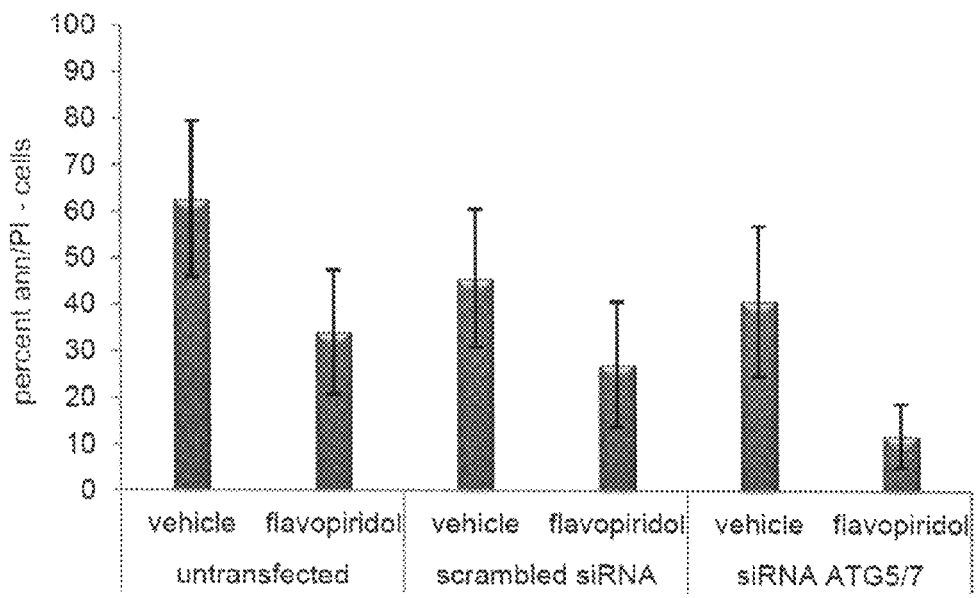
Figure 10B:
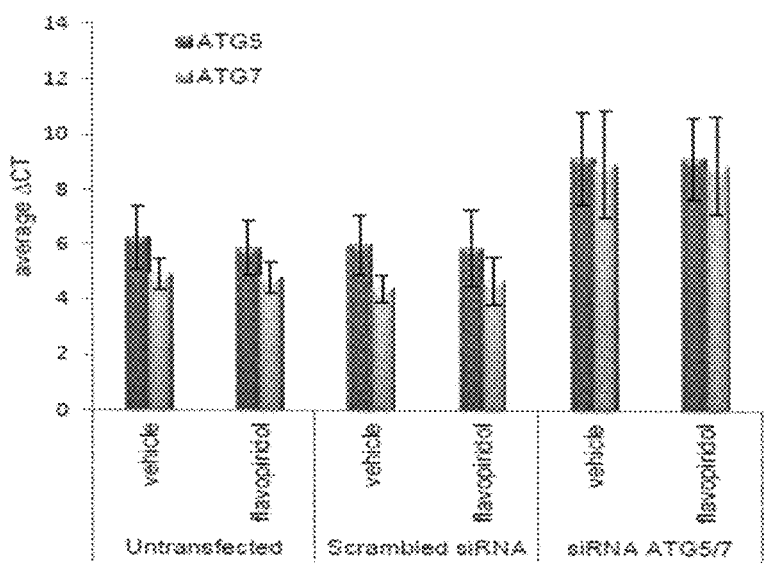

Inhibition of Autophagy Enhances Flavopiridol Cytotoxicity:

As shown FIG. 4A, co-treatment with chloroquine significantly enhances the cytotoxicity of flavopiridol in CLL cells (n=15; P=0.001). As chloroquine could affect other cell processes in addition to autophagy, we next tested if knock-down of ATG5/ATG7 by siRNA enhanced flavopiridol cytotoxicity. Following ATG5/ATG7 knock-down by transfection of cells with combination of siRNA to ATG5 and to ATG7 (FIG. 10B), flavopiridol-mediated cell death was significantly increased (P=0.004) (FIG. 4B) as previously observed with thapsigargin.

Figure 5:
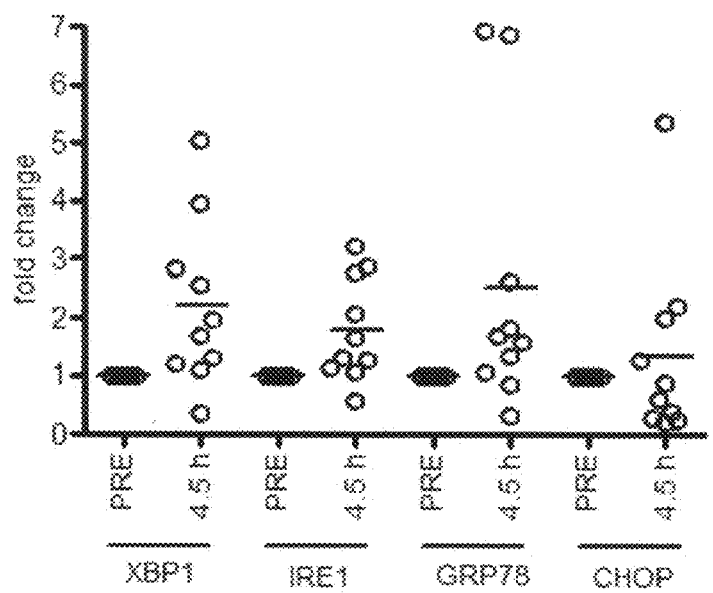
FIG. 5: Flavopiridol induces endoplasmic reticulum stress in CLL cells. Real-time RT-PCR for XBP1, IRE1, GRP78 and CHOP in CLL cells (n=10) collected from patients undergoing flavopiridol treatment (P values were calculated for comparisons between gene expression in pre-treatment samples versus samples collected at the end of infusion –4.5 hour. P=0.0008 for IRE1, P=0.0016 for XBP1, P=0.033 for GRP78). For all real-time RT-PCR experiments described here and in the following figures, CD52 was used as control housekeeping gene.
Figure 12A:
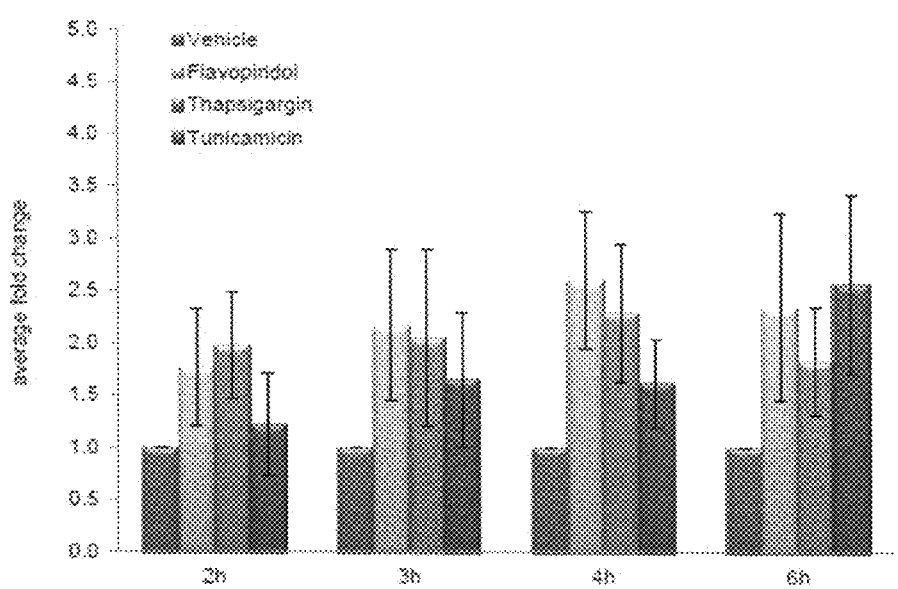
FIGS. 12A-12F: ER stress markers in CLL cells treated with flavopiridol. Real-time RT-PCR was used to analyze expression of (FIG. 12A) XBP1, (FIG. 12B) GRP78 and (FIG. 12C) IRE1 in CLL cells (n=5) incubated with flavopiridol 2 µM, thapsigargin 1 µM and tunicamycin 3 µg/ml. P values were calculated for vehicle versus each reagent used and they were as follows: for IRE1: P=0.008 for flavopiridol, P=0.005 for thapsigargin, P=0.003 for tunicamycin; for XBP1: P=0.053 for flavopiridol, P=0.077 for thapsigargin, P=0.099 for tunicamycin; for GRP78: P=0.038 for flavopiridol, P=0.012 for thapsigargin, P=0.062 for tunicamycin.
Figure 12B:
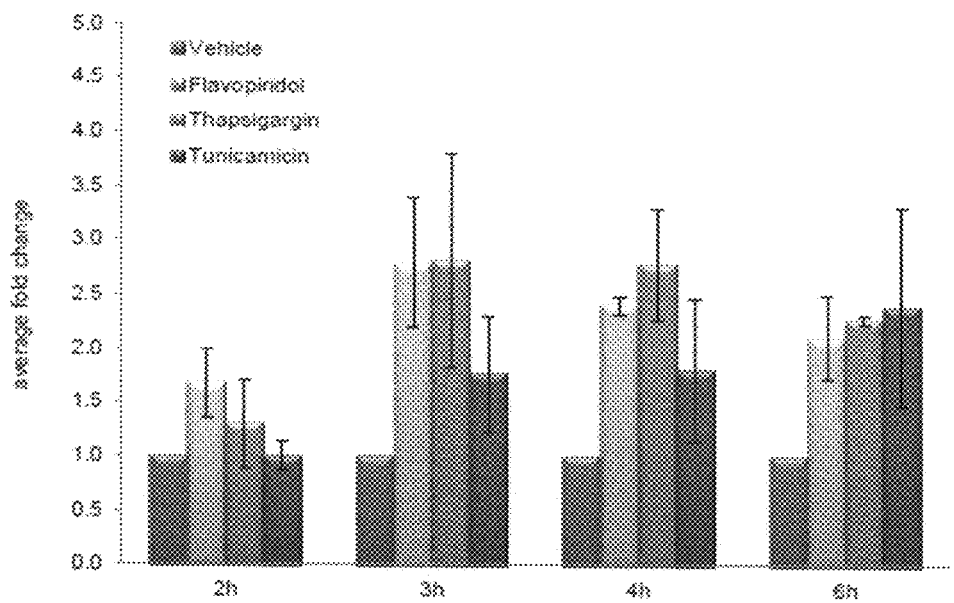
Figure 12C:
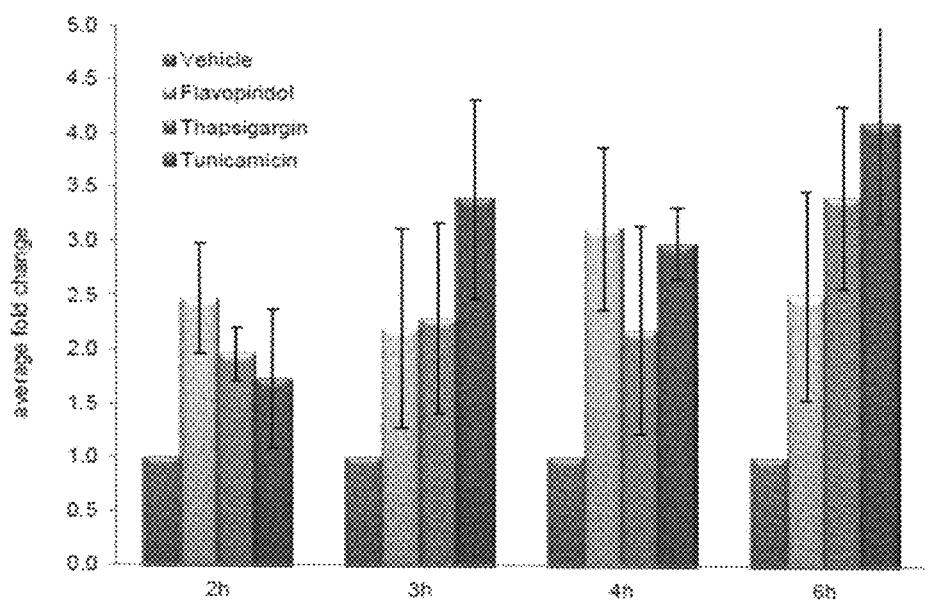
Figure 12D:
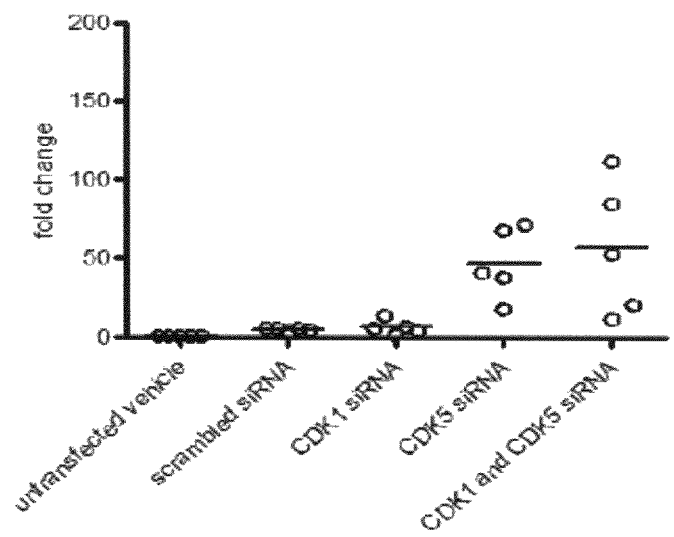
Figure 12E:
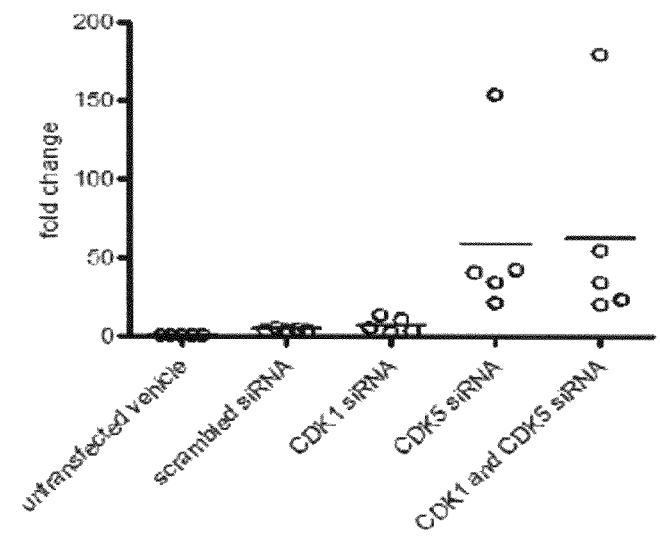
Figure 12F:
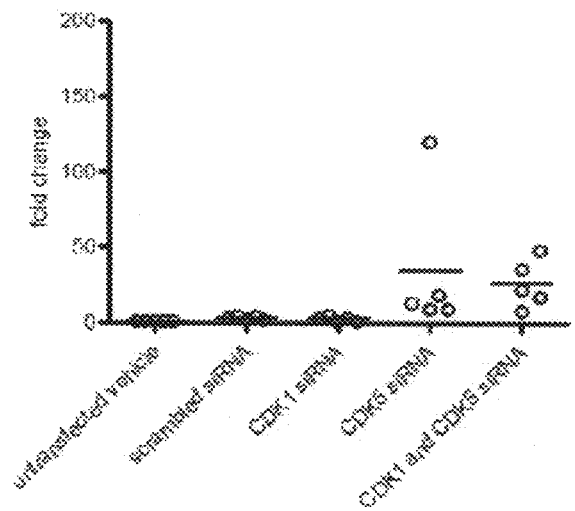

Flavopiridol Induces ER Stress in CLL Cells In Vitro and In Vivo:

As flavopiridol-treated CLL cells show an autophagy induction pattern similar to ER stress agents, the inventors herein now believe that flavopiridol induces ER stress, a mechanism of action not previously ascribed to CDK inhibitors. The inventors observed a significant, time-dependent increase in expression of ER stress genes XBP1, IRE1 and GRP78 in CLL cells treated with flavopiridol as well as the ER stress-inducing agents thapsigargin and tunicamycin (FIGS. 12A-12C). These same changes were not noted with F-ara-A. Importantly, significant increases in XBP1, IRE1 and GRP78 genes were also observed in samples obtained from CLL patients receiving flavopiridol in the clinic (n=10; P=0.0008 for IRE1, P=0.0016 for XBP1, P=0.033 for GRP78) but not in CHOP (P=0.292) (FIG. 5). To determine if the ER stress induced by flavopiridol in CLL cells is due to CDK5 inhibition, CLL cells were transfected with siRNA to CDK5. Compared to the scrambled control, CDK5 siRNA transfection resulted in increased expression of XBP1, GRP78 and IRE1, as was observed in cells incubated with flavopiridol (FIGS. 12D-12F). For all real-time RT-PCR experiments, the inventors we used CD52 as control housekeeping gene, as its levels are constant in the presence of all reagents used, in contrast to GAPDH or TBP, which showed significant variability in the presence of flavopiridol.

Figure 13A:
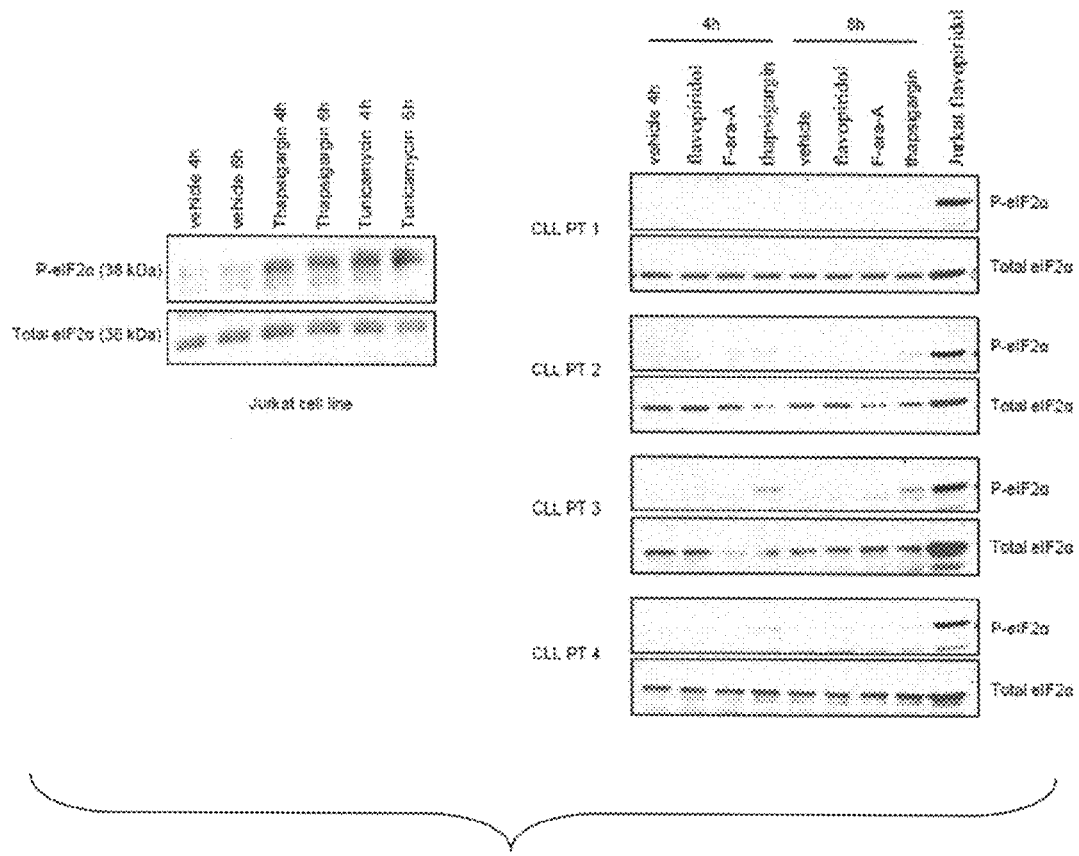
FIGS. 13A-13B: PERK and IRE1 activity in CLL cells.
Figure 13B:
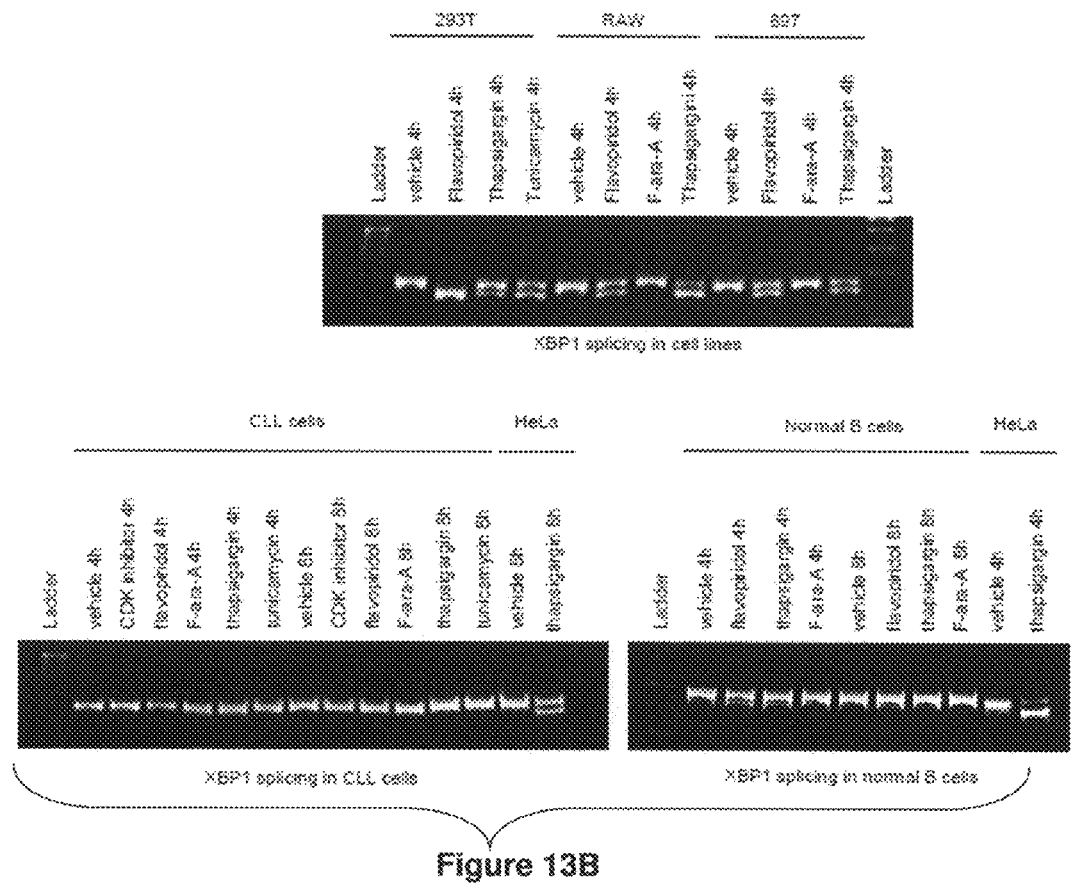

ER Stress Response in CLL Cells is Dysfunctional:

Since the initial ER stress studies in CLL cells showed that one of the ER stress markers, CHOP, does not increase like the other markers examined, the inventors further characterized this pathway in CLL cells. The inventors examined the activity of the unfolded protein response (UPR) initiators PERK, IRE1, and ATF6. PERK was minimally active following thapsigargin and flavopiridol treatment, as assessed by phosphorylation of its downstream target eIF2α. As a control, cell lines treated with flavopiridol or thapsigargin showed dramatic EIF2α phosphorylation (FIG. 13A). Similarly, no evidence of IRE1 activity was noted following flavopiridol or thapsigargin treatment, as determined by a general deficiency in splicing of the IRE1 substrate XBP1 (8 of 10 CLL samples tested). Furthermore, neither thapsigargin nor tunicamycin induced XBP1 splicing in any of the samples analyzed (FIG. 13B). In contrast, B cells from healthy donors and multiple cell lines (HeLa, 293T, RAW 264.7, 697) treated with flavopiridol or ER stress inducers showed XBP1 splicing. This finding shows a lesion in the UPR machinery in CLL cells.

Figure 6A:
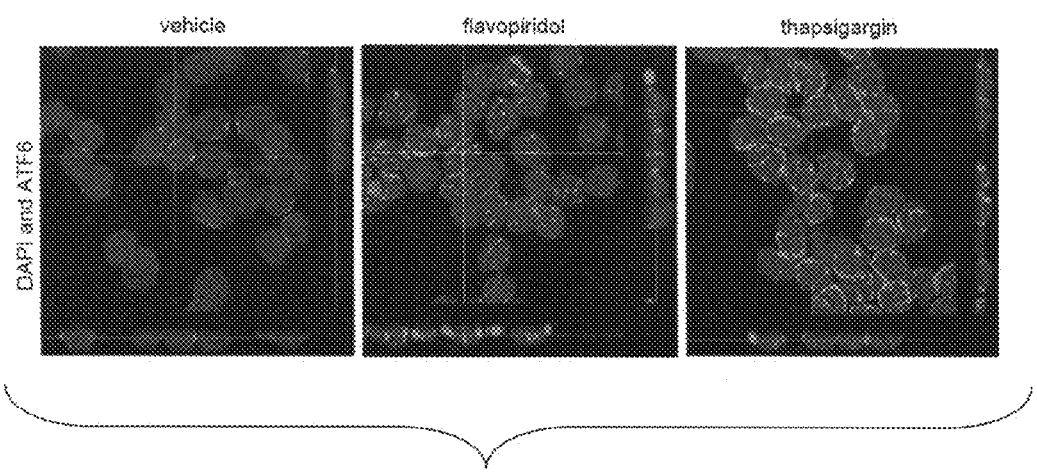
FIGS. 6A-6G: Endoplasmic reticulum stress in CLL cells.
Figure 6B:
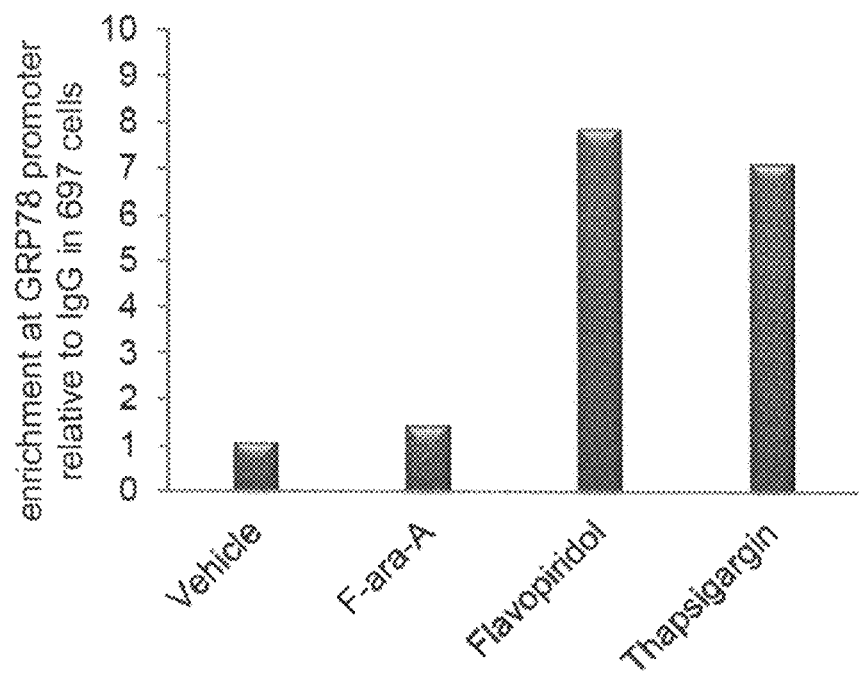
Figure 6C:
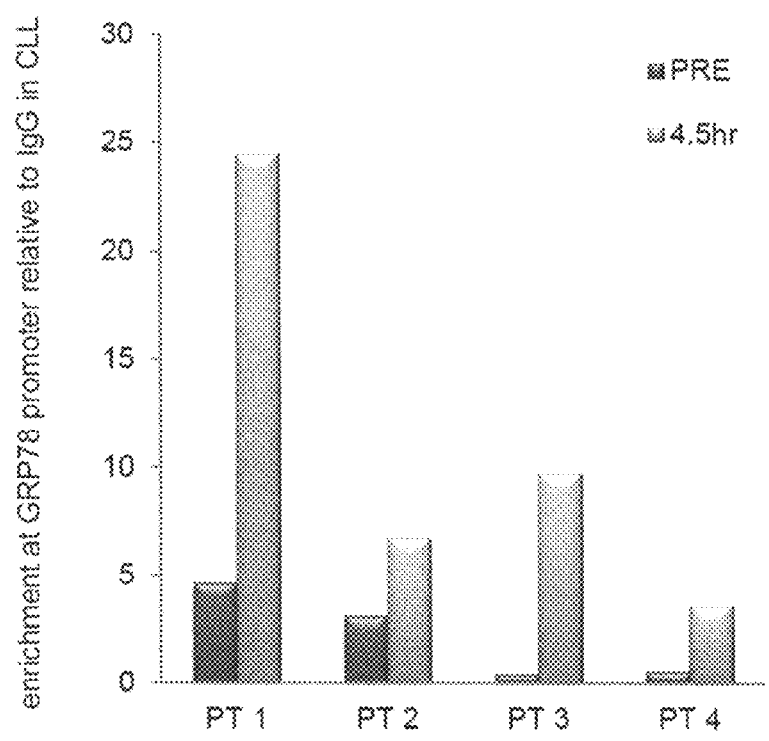

While PERK activation and XBP1 splicing were not observed, the increases in XBP1, IRE1 and GRP78 expression in vitro and in vivo show that part of the UPR is activated with flavopiridol. GRP78 transcription is induced by ATF6, a transcription factor which translocates to the nucleus in the presence of ER stress (49). ATF6 nuclear translocation was therefore examined by confocal fluorescence microscopy. As shown in FIG. 6A, increased nuclear translocation is observed in flavopiridol- or thapsigargin-treated CLL patient cells. This was complemented by enhanced binding of the GRP78 promoter region by ATF6, as determined by ChIP assay using anti-ATF6 antibody vs. a nonspecific (IgG) control in 697 cells treated with flavopiridol or thapsigargin (FIG. 6B). This increased promoter binding was not noted with F-ara-A. Importantly, results were similar in samples from CLL patients obtained before and 4.5 hour after flavopiridol infusion (FIG. 6C).

Figure 6D:
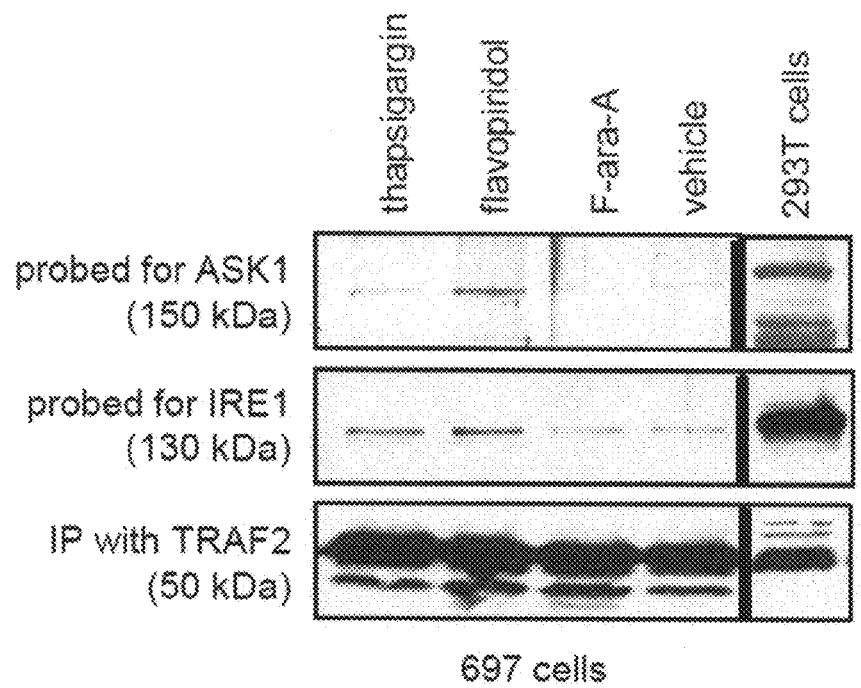
Figure 6E:
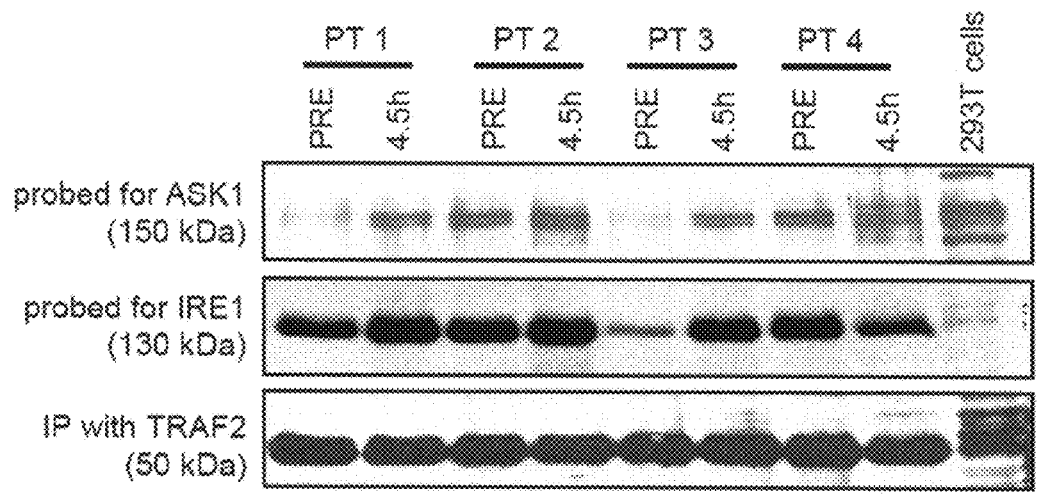
Figure 6F:
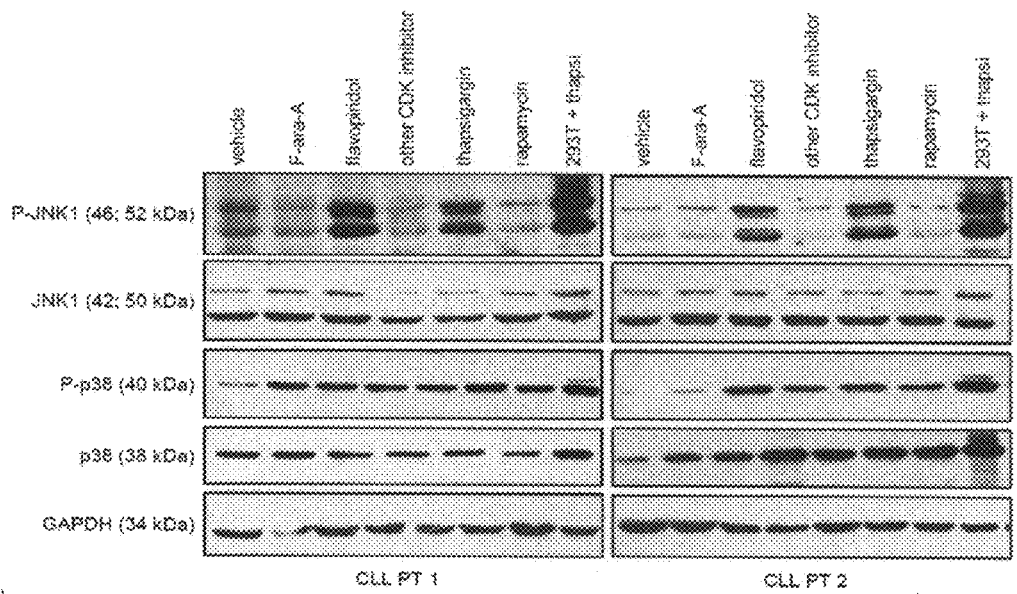
Figure 6G:
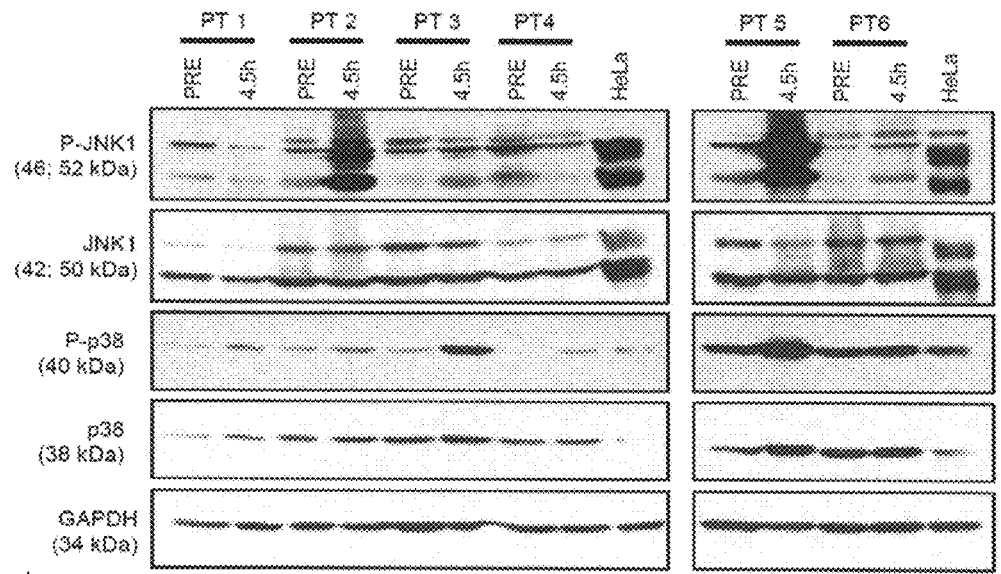

In addition to ATF6 nuclear translocation and GRP78 transcriptional induction, another early event of UPR is the formation of a complex between IRE1, the adaptor molecule TRAF2, and the MAP kinase pathway member ASK1. The inventors detected the formation of this complex by increased levels of ASK1 and IRE1 protein in TRAF2 co-immunoprecipitates in 697 cells treated with flavopiridol, and to a lesser extent with thapsigargin, as shown in FIG. 6D. This same increase in IRE1 and ASK1 association with TRAF2 is noted in CLL patient cells in vivo following flavopiridol infusion (FIG. 6E). Direct downstream effects of IRE1-TRAF2-ASK1 complex activity include phosphorylation of JNK1 and p38MAPK. Flavopiridol and thapsigargin treatment induced the phosphorylation of both JNK1 and p38MAPK in CLL cells, whereas F-ara-A did not (FIG. 6F). Moreover, JNK1 and p38MAPK phosphorylation was observed in five of ten CLL patients in samples obtained 4.5 hours following flavopiridol infusion (FIG. 6G). While the cause of the JNK1 and p38MAPK phosphorylation variability among these clinical samples is unclear, the inventors herein now believe that variations in sample processing could contribute to these results.

Figure 7A:
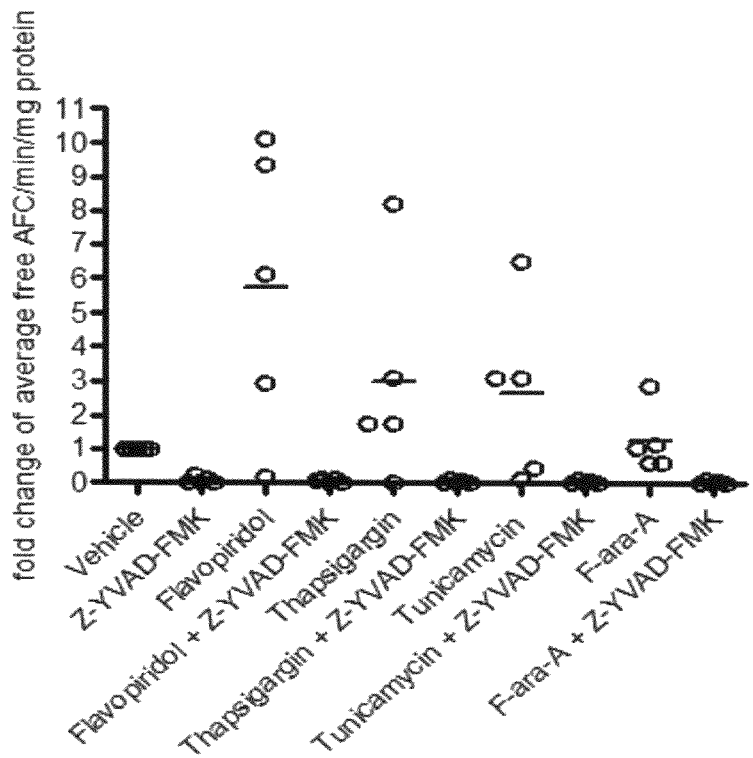
FIGS. 7A-7B: Markers of cell death by endoplasmic reticulum stress. Activity of caspase 4 (FIG. 7A) and caspase 8 (FIG. 7B) in CLL cells (n=5) treated in vitro with flavopiridol (2 µM), thapsigargin (1 µM), tunicamycin (3 µg/ml) or F-ara-A (5 µM) alone or in combination with caspase 4 inhibitor Z-YVAD-FMK (20 µM). Cells were incubated with flavopiridol 4 hours, washed, and re-plated in fresh media without drug; all the other reagents were left with the cells for 24 hours. Activity is shown as free AFC/min/mg protein (fluorescence released by cleaved substrate). Caspase 4 and 8 activity was significantly increased by each agent in the absence of Z-YVAD-FMK (P=0.0001).
Figure 7B:
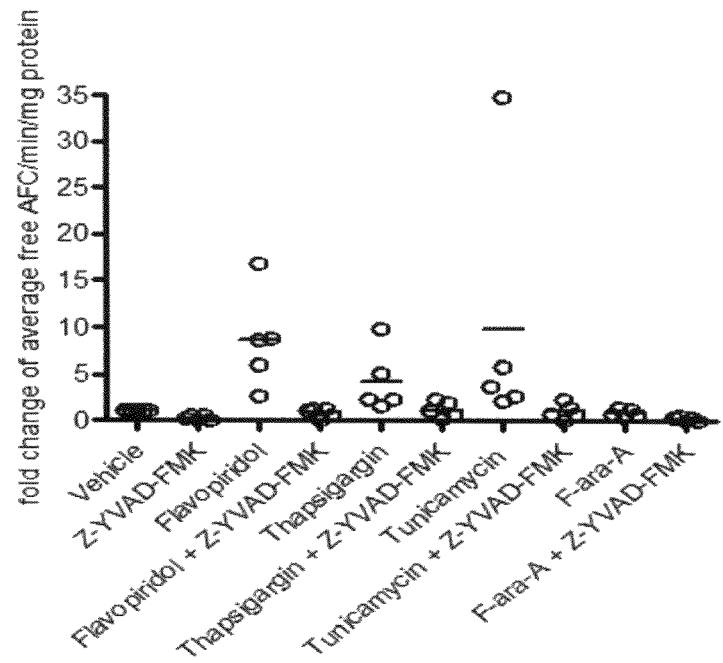
Figure 7C:
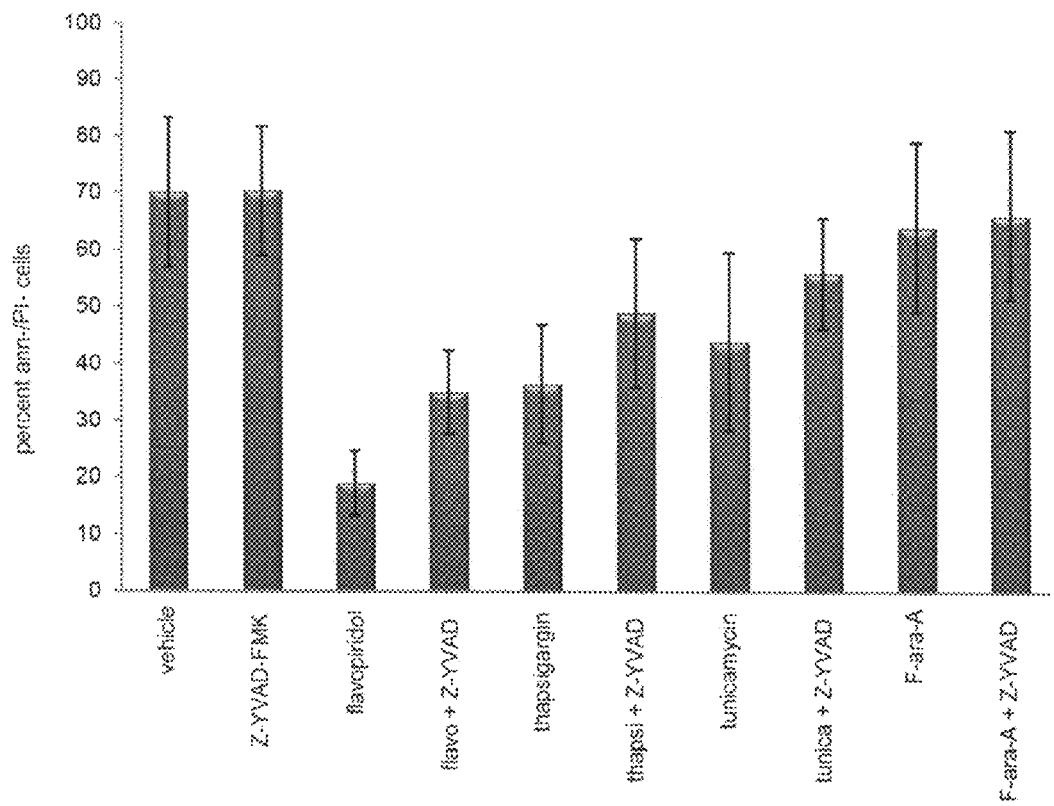
FIG. 7C: Viability of CLL cells from FIG. 7A and FIG. 7B, (n=5). Viability is shown as percent cells negative for both annexin and PI by flow cytometry at 24 hours. Z-YVAD-FMK significantly blocked flavopiridol-mediated cell death (P=0.012).
Figure 7D:
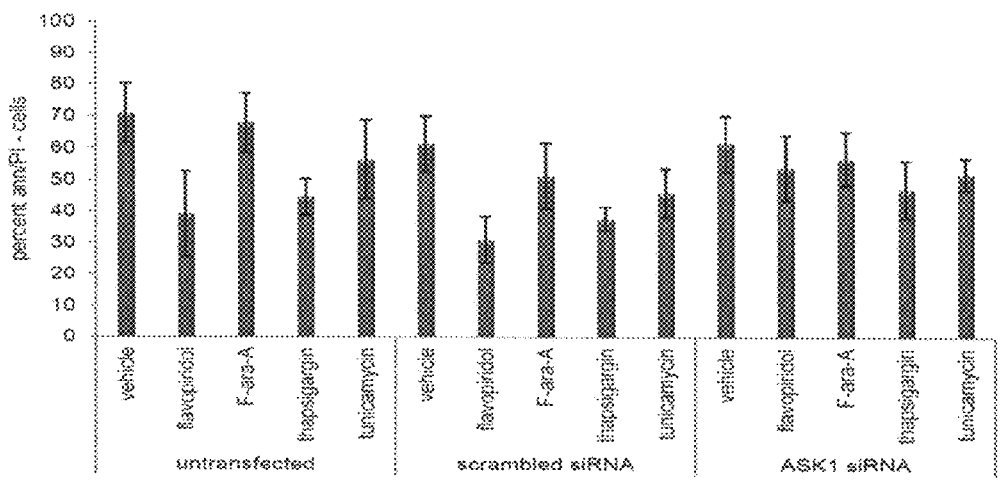
FIG. 7D: Viability of CLL cells (n=5) untransfected or transfected with scrambled or ASK1 siRNA, then treated with flavopiridol (2 µM), F-ara-A (5 µM), thapsigargin (1 µM), or tunicamycin (3 µg/ml) 24 hour after transfection. Flavopiridol cytotoxicity decreased in the presence of ASK1 siRNA (P=0.0005).
Figure 8:
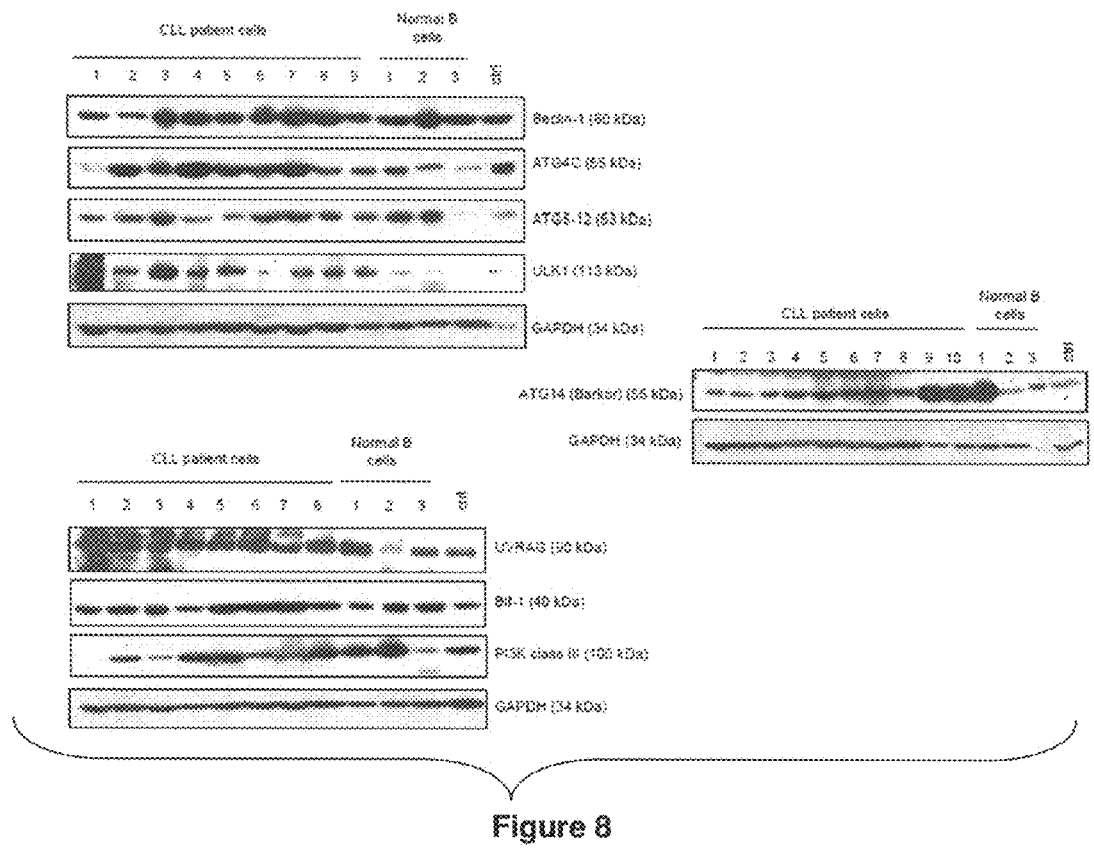
FIG. 8: Autophagy markers in CLL cells. Immunoblot showing autophagy regulatory protein expression in CLL cells and normal B cells; Gapdh was used as loading control.
Figure 14A:
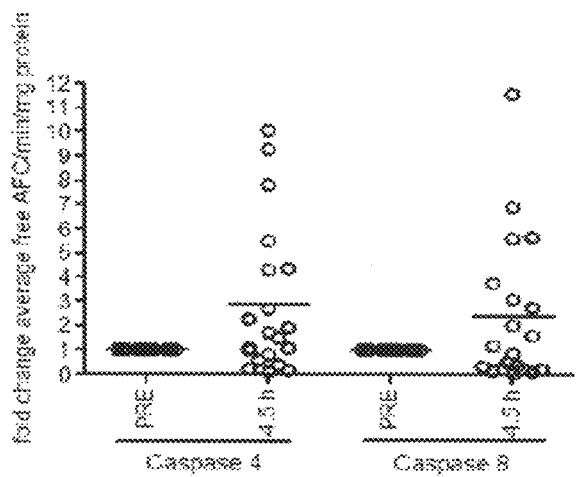
FIGS. 14A-14C: Markers of cell death by ER stress.
Figure 14B:
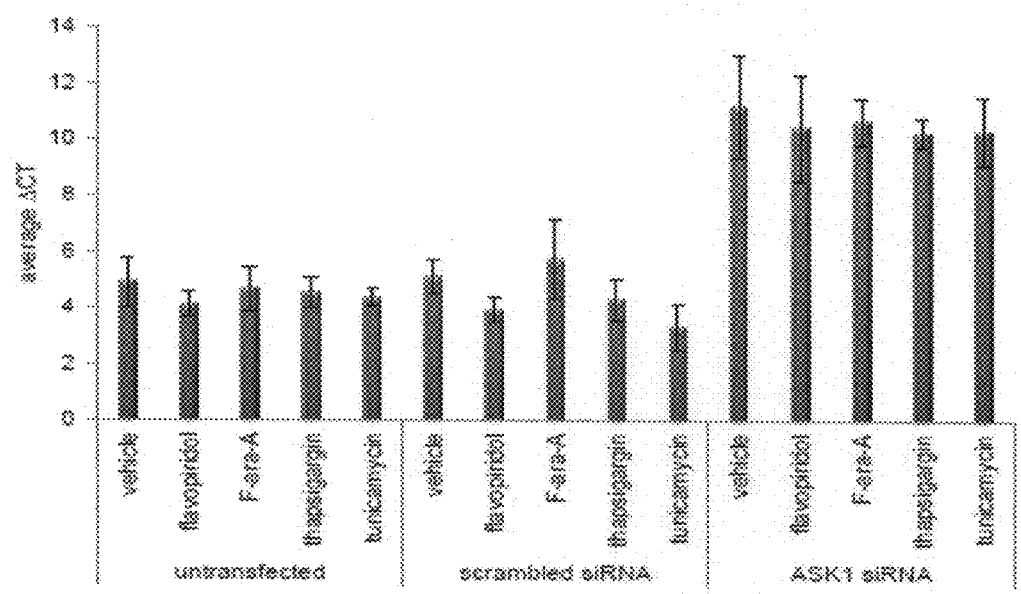
Figure 14C:
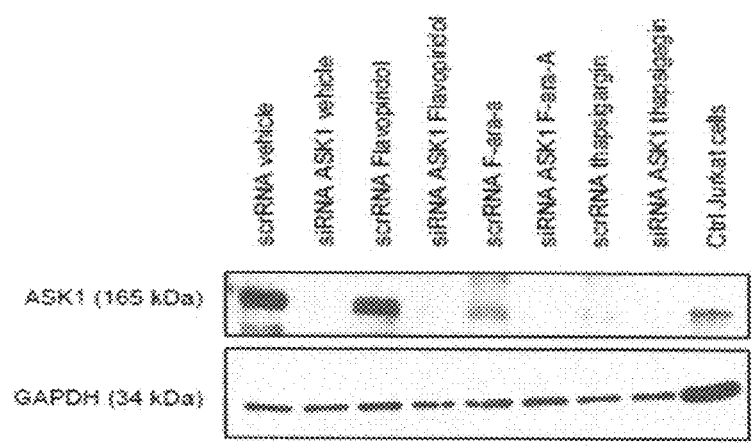

ER Stress Induced by Flavopiridol as a Mechanism of Cell Death:

During ER stress-mediated cell death, ASK1 activates caspase 4. To determine if the flavopiridol-induced IRE1-TRAF2-ASK1 complex contributes to cell death, the inventors determined studies caspase 4 and its downstream target caspase 8. In CLL cells incubated with flavopiridol, thapsigargin or tunicamycin, caspase 4 and 8 activity increased 5- to 10-fold (n=5; P=0.0001) compared to cells incubated with vehicle or F-ara-A (FIGS. 7A, B). This increased caspase activity was successfully inhibited by the caspase 4 inhibitor Z-YVAD-FMK. Moreover, flavopiridol-mediated cell death was significantly (P=0.012) reduced in the presence of Z-YVAD-FMK (FIG. 7C). In samples from CLL patients treated with flavopiridol in the clinic, 13 of 20 showed at least a two-fold increase in the activity of caspases 4 and 8 at 4.5 hours following flavopiridol infusion (FIG. 14A). To confirm the contribution of ASK1 activation to this process, cells were transfected with siRNA directed to ASK1 (efficacy shown in FIGS. 14B, 14C). These cells were significantly (P=0.005) more resistant to flavopiridol treatment than cells transfected with scrambled siRNA (FIG. 7D). Collectively, these findings indicate that ER stress, via the IRE1-ASK1-JNK1-caspase 4 cascade, is an important component of the mechanism of CLL cell death by flavopiridol.

Amelioration of Flavopiridol Induced Tumor Lysis (TLS)

It is recognized that administration of flavopiridol can cause serious tumor lysis. As such, it is within the contemplated scope of the present invention that such invention includes a method for treating subjects with the combination therapy described herein to those subjects who are not super sensitive to this CDK inhibitor.

For example, the data show that those subjects who are not responsive to flavopiridol alone may be converted to a response with modification of the dose of flavopiridol or the combination of flavopridol plus chloroquine.

It is to be further understood that the administration of such combination therapy can be administered using appropriate criteria for receiving flavopiridol to avoid excessive TLS. Further, the present combination therapy can be administered using specific regimens for dealing with the serious consequences of hyper-acute TLS should it occur.

Discussion of Example 1

Example 1 documents that primary CLL cells express the critical components of the autophagy machinery, and that autophagy can be robustly activated in these cells by commonly reported stimuli and also select CLL therapeutics including fludarabine, CAL-101, and flavopiridol. Unexpectedly, the induction of autophagy offered little protection from cell death from most stimuli, including fludarabine and CAL-101. Flavopiridol and the ER stress-inducing agent thapsigargin were notable exceptions, where either pharmacologic or siRNA-mediated inhibition of autophagy enhanced cytotoxicity.

Example 1 also demonstrates that flavopiridol does in fact mediate robust ER stress in CLL cells, but that this process is dysfunctional compared to normal B-cells as characterized by absence of PERK activation and XBP1 splicing. Nonetheless, flavopiridol-induced ER stress promotes cell death via IRE1-induced activation of ASK1 and caspase 4. Notably, activation of autophagy, ER stress, and downstream activation of caspase 4 was demonstrated in samples obtained from CLL patients receiving flavopiridol treatment. These collective findings document for the first time that CDK inhibitors promote ER stress, and also identify autophagy as a mechanism of CDK inhibitor resistance that can be therapeutically targeted in resistant tumors.

In addition to identifying new mechanisms of action and resistance for CDK inhibitors, Example 1 further shows the first systematic investigation of autophagy in CLL with multiple inducers of this process. These results demonstrate that many stimuli, including common therapeutic agents, can promote autophagy in CLL tumor cells. However, for most of these stimuli, disruption of autophagy does not enhance cell death. Agents that induce ER stress proved an exception to this, indicating that for ER stress mediated killing, the process of autophagy is a relevant resistance mechanism.

This is of importance since autophagy is a mechanism of drug resistance. Notably, each of the agents identified were shown to be inducers of ER stress. These findings collectively show the usefulness of combination strategies with CDK inhibitors, and other ER stress inducers, with inhibitors of autophagy to enhance therapeutic benefit.

Example 1 further demonstrates that knockdown of CDK5 expression results in both induction of autophagy and increase in ER stress genes in CLL cells. ER stress is a natural cellular response to a variety of stimuli that leads to the unfolded protein response (UPR) involving: a) IRE1 activation that leads to XBP1 mRNA splicing; b) ATF6 release from the ER membrane, followed by nuclear translocation and transcriptional up-regulation of ER response genes; and c) PERK activation and phosphorylation of EIF2α, which leads to the inhibition of translation initiation (61). With continued ER stress, terminal UPR events occur that include release of ER-sequestered calcium, IRE1 association with TRAF2 and ASK1, and subsequent activation of multiple pro-apoptotic processes that ultimately lead to cell death.

The data in Example 1 show that in CLL, but not normal B-cells or cell lines, the ER stress response is only partially functional as demonstrated by absence of XBP1 splicing and PERK activation. However, following treatment with flavopiridol or thapsigargin, CLL cells demonstrate ATF6 nuclear translocation and binding to GRP78 promoter as well as formation of the IRE1/TRAF2/ASK1 complex and activation of JNK1, p38, and caspase 4.

The importance of the IRE1/TRAF2/ASK1 complex formation and downstream caspase 4 activation to flavopiridol cell death is demonstrated by both ASK1 siRNA knockdown and also caspase 4 inhibition, both of which antagonize flavopiridol-induced cell death. The clinical relevance of these in vitro findings was confirmed by examination of cells from patients receiving flavopiridol, in which these same biochemical events were noted.

The complex network of signals induced by flavopiridol-mediated ER stress thus provides novel approaches to enhance CDK inhibitor efficacy in CLL, and other cancers as well.

Specifically, therapeutics such as chloroquine that block the autophagic process may convert a CDK inhibitor-resistant case to a responsive one. Notably, the tests with chloroquine were performed using concentrations that are physiologically attainable in patients receiving treatment for malaria.

In other embodiments, the present invention is also useful to interfere with autophagy by targeting ATG family members, ATG4 members or the Vps34/Beclin1/Barkor complex.

Similarly, these results support the development of strategies to enhance activation of the late UPR response, including IRE1/TRAF2/ASK1 complex formation and activation of caspase 4.

Given that thioredoxin directly binds to ASK1 and prevents its inclusion in this complex, pharmacologic agents depleting thioredoxin represent an attractive potential combination.

Regardless, the clinical potential of CDK inhibitors in CLL and other malignancies cannot be ignored, and efforts focused on combination therapies targeting the autophagy and UPR networks will help to optimize their application in the treatment of cancer.

Materials and Methods for Example 1

Patients, Cell Separation, Culture Conditions and Reagents:

For both in vivo and in vitro studies, written, informed consent was obtained to procure cells from patients with previously diagnosed CLL as defined by the modified National Cancer Institute (NCI) criteria. CD19-positive cells from CLL patients and normal volunteers were selected and maintained in culture.

Flavopiridol was obtained from the NCL Rapamycin was purchased from EMD-Calbiochem (Gibbstown, N.J.). BAPTA/AM, chloroquine, thapsigargin, F-ara-A ((9-β-D-arabinofuranosyl-2-fluoroadenine 5'-phosphate), chlorambucil and tunicamycin were obtained from Sigma-Aldrich (St. Louis, Mo.), rituximab from Genentech (San Francisco, Calif.), and CAL-101 from Calistoga Pharmaceuticals (Seattle, Wash.).

Confocal Immunofluorescence Microscopy of Fixed Cells:

After 4 hours exposure to agents, cells were washed in phosphate-buffered saline (PBS) and made adherent on a microscope slide by centrifugation in a Cytospin3 (Shandon) centrifuge. Immediately after cytospin, cells were fixed in cold acetone. Next, the cells were incubated in blocking solution (2% bovine serum albumin in PBS) and stained for LC3 (Cell Signaling, Boston, Mass.)) and Lamp2 (Santa Cruz Biotechnology, Santa Cruz, Calif.) by incubating separately with the respective primary antibodies over night, in 4° C., followed by incubation with fluorescent secondary antibodies (Invitrogen, Carlsbad, Calif.): Alexa fluor 594 (red) anti-rabbit for LC3 and Alexa fluor 488 (green) anti-mouse for Lamp2. Nuclei were stained blue with DAPI (Vector Laboratories, Burlingame, Calif.). Images were taken using a 60× objective and 4× digital zoom with Olympus Fluoview 1000 Laser Scanning Confocal microscope at the Ohio State University Campus Microscopy and Imaging Facility. ATF6 antibody was purchased from LifeSpan Biosciences (Seattle, Wash.) and Nrf2 was from Santa Cruz Biotechnology (Santa Cruz, Calif.). Nuclei were evaluated for ATF6 and Nrf2 using confocal microscopy to collect Z stacks, approximately 45 slices per cell, 0.2 µm each.

Quantification of Immunofluorescence Data:

LC3 intensity and number of dots per cell were both assessed in the fluorescence images. Integrated intensity was measured using Metamorph v.7.0. To calculate the number of "dots" (local extreme point in pixel-intensity profile at which a number of high-intensity pixels form a cluster), a Gaussian filter was first applied to reduce noise. Cells were enumerated electronically by an improved watershed-based algorithm. To quantify co-localization, two binary nuclei images—red (R) and green (G)—are obtained. The correlation value is calculated as the number of white pixels of (R&G) divided by the number of pixels of (R|G), where (R&G) is the intersection of R and G, and (R|G) is the union of R and G. The program used for cell counts and measurement of correlation index is based on MatLab software (Natick, Mass.) and it was developed by members of Department of Biomedical Informatics, The Ohio State University.

Immunoblot Analysis and Co-immunoprecipitation:

Proteins extracted from whole cell lysates (50 µg/lane) were separated on polyacrylamide gels and transferred on nitrocellulose membrane. Antibodies used for immunoblots included LC3, IRE1α, TRAF2, PI3K III, ATG4C, ATG5-12, UVRAG, Beclin-1 (Cell Signaling, Boston, Mass.), GAPDH, Nrf2, ASK1, ULK1 (Santa Cruz Biotechnology), and Bif-1, ATG14-Barkor (Sigma-Aldrich, St Louis, Mo.). Species-appropriate secondary antibodies were obtained from BioRad Laboratories (Hercules, Calif.). Following antibody incubations, proteins were detected using a chemiluminescent substrate (BioRad Laboratories). For co-immunoprecipitations, TrueBlot beads (eBiosciences, San Diego, Calif.) and One-hour IP Western kit (GenScript, Piscataway, N.J.) were used according to manufacturer protocols. Quantification was done using FluorChem Q (Alpha Innotech, San Leandro Calif.).

Caspase Activity Assays:

The presence of active caspase enzymes was determined by the AFC assay. Briefly, lysates containing approximately $3 \times 10^6$ cells were incubated with 50 µM LEVD-AFC (caspase 4 substrate) or LETD-AFC (caspase 8 substrate) from MP Biomedicals (Solon, Ohio) in 2× cytobuffer from BioVision (Exton, Pa.) containing 10 mM dithiothretiol (DTT). Caspase 4 activity was measured one hour after addition of substrate and caspase 8 activity was measured 30 minutes after addition of substrate. Release of free AFC was measured with a Beckman-Coulter DTX 880 multimode detector (Filters: excitation, 405/10 nm; emission, 535/25 nm). Caspase 4 inhibitor Z-YVAD-FMK was purchased from R&D Systems.

Cell Viability:

Percent of live cells was determined by staining with annexin V-fluorescein isothiocyanate and propidium iodide (PI). After exposure to agents, cells were washed with PBS and stained in 1× binding buffer (BD Biosciences, Franklin Lakes, N.J.). Cell viability was assessed by flow cytometry using a Beckman-Coulter Cytomics FC500 cytometer. Data were analyzed with the CXP Cytometer software package (Beckman-Coulter). A total of 10,000 cells were counted for each sample. The cells treated with flavopiridol were washed after 4 hours with PBS and re-suspended in regular growth medium (RPMI 1640) supplemented with 10% human serum and antibiotics for the remainder of the incubation time. In the case of flavopiridol/chloroquine samples, chloroquine was re-added in the fresh media after flavopiridol was washed at 4 hours. For all the other conditions, cells were incubated with the respective drugs for 24 hours continuously.

siRNA Experiments:

CLL cells were suspended in buffer V (Amaxa kit, Lonza, Allendale, N.J.) and nucleofection was performed using program U016 (5 μg siRNA and $1 \times 10^7$ cells per cuvette). Scrambled siRNA and siRNAs to ATG5, ATG7 and ASK1 were purchased from Sigma-Aldrich. Cells were immediately suspended in warm, complete media supplemented with 10% human serum, and RNA was extracted after 36 hours. For CDK1 and CDK5, siRNAs were purchased from Applied Biosystems (Carlsbad, Calif.). Transfections were done using 5 nM siRNA per cuvette, and RNA was harvested at 48 hours.

ChIP Assays:

EZ Magna ChIP kit from Millipore (Billerica, Mass.) was used according to the protocol suggested by the manufacturer. In brief, cells were treated with 37% formaldehyde to ensure crosslinking of proteins to DNA. Cells were lysed and sonicated to shear the chromatin to fragments of approximately 500 bp. Sheared chromatin was incubated with ATF6 antibody (LifeSpan Biosciences, Seattle, Wash.), followed by precipitation, washing and reversing of the crosslinks Purified DNA was then analyzed by real-time quantitative PCR using primers to the GRP78 promoter region. Primers were designed using Primer 3 software and purchased from IDT (Coralville, Iowa).

PCR and Real-Time Quantitative PCR:

RNA was extracted using TRIzol reagent (Invitrogen, Carlsbad, Calif.) and purified using QIAGEN RNeasy columns (Qiagen, Valencia, Calif.). cDNA was prepared with SuperScript First-Strand Synthesis System (Invitrogen). Real-time PCR was performed using primers purchased from Applied Biosystems. Detection was performed using an ABI Prism 7700 sequence detection system (Applied Biosystems). Average relative expression (treatment compared with vehicle) was normalized to the internal control gene CD52. Primers to detect spliced XBP1 were designed using Primer 3 software and purchased from IDT. Samples were analyzed on 10% acrylamide gels.

Statistical Analyses:

Data from experiments involving quantification of fluorescence in vitro data, RT-PCR, viability measured by flow cytometry and caspase assays were first log-transformed to stabilize variances. Next, linear mixed effects models were applied to the log-transformed data in order to account for the correlations among observations from the same patients. Holm's procedure was used to adjust for multiple comparisons and control overall Type I error.

For the quantification of LC3 fluorescence in serial samples (in vivo data), CLL patients were classified as either "no response" (N=10) or "partial response" (N=6). Similar to above, data from both experiments were log-transformed, and a linear mixed effects model was applied to the log-transformed data. The significance of the interaction between response category and time was tested. All analyses were performed using SAS/STAT version 9.2 (SAS Institute Inc., Cary, N.C., USA).

Example 2

As used herein, unless clearly indicated otherwise, the term "an individual" intends a mammal, including but not limited to a human. The individual may be a human who has been diagnosed with or is suspected of having or is at risk of developing a lymphoproliferative disease. The individual may be a human who exhibits one or more symptoms associated with a lymphoproliferative disease. The individual may be a human who is genetically or otherwise predisposed to developing a lymphoproliferative disease. In one variation, the individual may be a human who has been diagnosed with or is suspected of having or is at risk of developing a lymphoproliferative disease. In one variation, the individual may be a human who exhibits one or more symptoms associated with a lymphoproliferative disease. In one variation, the individual may be a human who is genetically or otherwise predisposed to developing a lymphoproliferative disease.

For use herein, unless clearly indicated otherwise, the combination therapy may be administered to the individual by any available dosage form. The first agent and second agent of a combination therapy may be administered in the same or different dosage forms and the invention includes these various dosage forms. In one variation, the first agent or the second agent or both the first agent and the second agent of a combination therapy is/are administered to the individual as a conventional immediate release dosage form. In one variation, the first agent or the second agent or both the first agent and the second agent of a combination therapy is/are administered to the individual as a sustained release form or part of a sustained release system, such as a system capable of sustaining the rate of delivery of the compound to an individual for a desired duration, which may be an extended duration such as a duration that is longer than the time required for a corresponding immediate-release dosage form to release the same amount (e.g., by weight or by moles) of compound, and can be hours or days. A desired duration may be at least the drug elimination half life of the administered compound and may be, e.g., at least about 6 hours or at least about 12 hours or at least about 24 hours or at least about 30 hours or at least about 48 hours or at least about 72 hours or at least about 96 hours or at least about 120 hours or at least about 144 or more hours, and can be at least about one week, at least about 2 weeks, at least about 3 weeks, at least about 4 weeks, at least about 8 weeks, or at least about 16 weeks or more.

The term "effective amount" intends such amount of a compound (e.g., a component of a combination therapy of the invention) or a combination therapy, which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. Standard methods can be used to measure the magnitude of this effect, such as in vitro assays with purified enzyme, cell-based assays, animal models, or human testing. An effective amount of a combination therapy includes an amount of the first compound and an amount of the second agent that, when administered sequentially, simultaneously, or continuously, produce a desired outcome.

In various embodiments, treatment with the combination therapy may result in an additive or even synergistic (e.g., greater than additive) result compared to administration of either the first agent or the second agent alone. In some embodiments, a lower amount of each of the first agent and the second agent is used as part of a combination therapy compared to the amount of each component generally used for individual (non-combination) therapy. Preferably, the same or greater therapeutic benefit is achieved using a combination therapy than using any of the individual compounds (combination components) alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. Preferably, the use of a smaller amount results in a reduction in the number, severity, frequency, or duration of one or more side-effects associated with that compound. Suitable doses of any of the compounds that are administered in conjunction with each other as part of the combination therapy may optionally be lowered due to the combined action (e.g., additive or synergistic effects) of the compounds.

The term "simultaneous administration," as used herein, means that a first agent and a second agent in a combination therapy are administered with a time separation of no more than about 15 minutes, such as no more than about any of 0, 5, or 1 minutes. When the compounds are administered simultaneously, the first agent and second agent may be contained in the same composition or in separate compositions.

As used herein, the term "sequential administration" means that the first agent and a second agent in a combination therapy are administered with a time separation of more than about 15 minutes, such as more than about any of 20, 30, 40, 50, 60 or more minutes. Either the first agent or the second agent may be administered first. The first agent and second agent for a sequential administration are contained in separate compositions, which may be contained in the same or different packages or kits.

A compound/component of the combination therapy may be formulated with suitable carriers for any available delivery route, whether in immediate or sustained release form, including oral, mucosal (e.g., nasal, sublingual, vaginal, buccal or rectal), parenteral (e.g., intramuscular, subcutaneous, or intravenous), topical or transdermal delivery. A compound may be formulated with suitable carriers to provide delivery forms, which may be but are not required to be sustained release forms, that include, but are not limited to: tablets, caplets, capsules (such as hard gelatin capsules and soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs. The first agent and second agent of a combination therapy may be formulated with suitable carriers for the same or different dosage routes and may be formulated for simultaneous administration via the same dosage route.

The first agent and second agent of a combination therapy can be used either separately or together in the preparation of a formulation, such as a pharmaceutical formulation, by combining the compound or compounds as an active ingredient with a pharmacologically acceptable carrier, which are known in the art. Depending on the therapeutic form of the system, the carrier may be in various forms. In addition, pharmaceutical preparations may contain preservatives, solubilizers, stabilizers, re-wetting agents, emulgators, sweeteners, dyes, adjusters, salts for the adjustment of osmotic pressure, buffers, coating agents or antioxidants. Preparations containing an active ingredient may also contain other substances which have valuable therapeutic properties. Therapeutic forms may be represented by a usual standard dose and may be prepared by a known pharmaceutical method. Suitable formulations can be found, e.g., in Remington's Pharmaceutical Sciences, Mack Publishing Company, Philadelphia, Pa., 20.sup.th ed. (2000), which is incorporated herein by reference.

The amount of a compound/component of the combination therapy in a delivery form may be any effective amount. In one variation, the combination therapy comprises the first agent in a dosage form in an amount from about 10 ng to about 1,500 mg or more. In one variation, the first agent in a dosage form comprises an amount from about 10 ng to about 1000 mg, from about 10 ng to about 500 mg, from about 10 ng to about 250 mg, from about 10 ng to about 100 mg, from about 10 ng to about 50 mg, from about 10 ng to about 25 mg, from about 10 ng to about 10 mg, from about 10 ng to about 5 mg, from about 10 ng to about 1 mg, from about 10 ng to about 500 µg, from about 10 ng to about 250 µg, from about 10 ng to about 100 µg, from about 10 ng to about 10µ, from about 10 ng to about 5 µg, from about 10 ng to about 1 µg, from about 10 ng to about 500 ng, from about 10 ng to about 250 ng, from about 10 ng to about 100 ng, from about 10 ng to about 50 ng, or from about 10 ng to about 50 ng. In one variation, the first agent in a dosage form comprises an amount from about 10 ng to about 1000 ng, from about 100 ng to about 500 ng, from about 500 ng to about 1000 ng, from about 1 µg to about 100 µg, from about 10 µg to about 1000 µg, from about 100 µg to about 500 µg, from about 500 µg to about 1000 µg, from about 1 mg to about 100 mg, from about 10 mg to about 100 mg, from about 50 mg to about 500 mg, from about 100 mg to about 500 mg, from about 100 mg to about 1000 mg, or from about 500 mg to about 1500 mg. In one variation, the combination therapy comprises the second agent in a dosage form in an amount of from about 10 ng to about 1,500 mg or more.

In one variation, the combination therapy comprises chloroquine as the first agent in a delivery form and flavopiridol as the second agent A treatment regimen involving a dosage form of the first agent and/or a second agent of a combination therapy, whether immediate release or a sustained release system, may involve administering the first compound and/or the second agent to the individual in a dose of between about 0.1 and about 10 mg/kg of body weight, at least once a day and during the period of time required to achieve the therapeutic effect. In other variations, the daily dose (or other dosage frequency) of the first agent and/or the second agent is between about 0.1 and about 8 mg/kg; or between about 0.1 to about 6 mg/kg; or between about 0.1 and about 4 mg/kg; or between about 0.1 and about 2 mg/kg; or between about 0.1 and about 1 mg/kg; or between about 0.5 and about 10 mg/kg; or between about 1 and about 10 mg/kg; or between about 2 and about 10 mg/kg; or between about 4 to about 10 mg/kg; or between about 6 to about 10 mg/kg; or between about 8 to about 10 mg/kg; or between about 0.1 and about 5 mg/kg; or between about 0.1 and about 4 mg/kg; or between about 0.5 and about 5 mg/kg; or between about 1 and about 5 mg/kg; or between about 1 and about 4 mg/kg; or between about 2 and about 4 mg/kg; or between about 1 and about 3 mg/kg; or between about 1.5 and about 3 mg/kg; or between about 2 and about 3 mg/kg; or between about 0.01 and about 10 mg/kg; or between about 0.01 and 4 mg/kg; or between about 0.01 mg/kg and 2 mg/kg; or between about 0.05 and 10 mg/kg; or between about 0.05 and 8 mg/kg; or between about 0.05 and 4 mg/kg; or between about 0.05 and 4 mg/kg; or between about 0.05 and about 3 mg/kg; or between about 10 kg to about 50 kg; or between about 10 to about 100 mg/kg or between about 10 to about 250 mg/kg; or between about 50 to about 100 mg/kg or between about 50 and 200 mg/kg; or between about 100 and about 200 mg/kg or between about 200 and about 500 mg/kg; or a dosage over about 100 mg/kg; or a dosage over about 500 mg/kg.

The combination therapy may be administered to an individual in accordance with an effective dosing regimen for a desired period of time or duration, such as at least about one month, at least about 2 months, at least about 3 months, at least about 6 months, or at least about 12 months or longer. In one variation, the combination therapy is administered on a daily or intermittent schedule for the duration of the individual's life.

Treatment Regimes

Combination therapies that include a first agent and a second agent may have enhanced activity for treating, preventing and/or delaying the onset and/or development of a lymphoproliferative disease. In particular, combination therapies of the invention include chloroquine or a pharmaceutically acceptable salt thereof in conjunction with a CDK inhibitor, such as flavopiridol, for treating, preventing and/or delaying the onset and/or development of a lymphoproliferative disease. Methods that use such combination therapies may result in an additive or even synergistic (e.g., greater than additive) result compared to administration of either compound of the combination therapy alone.

In one variation, a combination therapy comprising a first agent and a second agent requires lower doses of the individual agents than would be necessary if the individual agents were given alone. Thus, in some embodiments, a lower amount of each pharmaceutically active agent is used as part of a combination therapy compared to the amount generally used for individual therapy. In some embodiments, the same or greater therapeutic benefit is achieved using a smaller amount (e.g., a lower dose or a less frequent dosing schedule) of a pharmaceutically active compound in a combination therapy than the amount generally used for individual therapy. Preferably, the use of a small amount of pharmaceutically active compound results in a reduction in the number, severity, frequency or duration of one or more side-effects associated with any of the agents.

Kits

The first and second agents of a combination therapy may be combined with a pharmaceutically acceptable carrier, and pharmaceutical compositions comprising the combination therapy are intended.

The invention also embraces combination therapy unit dosage forms, where the first and second agents of a combination therapy are present in a unit dosage form. As used herein, the term "unit dosage form" refers to a combination therapy formulation that contains a predetermined dose of a first agent and a predetermined dose of a second agent. The first and second agents of the combination therapy unit dosage form are present in amounts effective to treat the disease for which they are prescribed.

The invention further provides kits comprising a combination therapy as described herein. The kits may contain the first and second agents of the combination therapy as a unit dosage form; e.g., the dosage form contains both the first and second agents; or, as discrete dosage forms (e.g., the first agent is contained in one dosage form and the second agent is contained in another dosage form). The kits will also contain instructions for use. In one variation, the kits comprise the first and second agents; and instructions for use of in the treatment, prevention, slowing the progression or delaying the onset and/or development of a disease.

Kits generally comprise suitable packaging. The kits may comprise one or more containers comprising any compound or combination therapy described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions are also acceptable, relating to the use of component(s) of the methods of the present invention (e.g., treating, preventing and/or delaying the onset and/or the development of a disease being treated. The instructions included with the kit generally include information as to the components and their administration to an individual.

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method of (a) treating a lymphoproliferative disease in a subject in need thereof; (b) slowing the progression of a lymphoproliferative disease in a subject who has been diagnosed with a lymphoproliferative disease; or (c) preventing or delaying development of a lymphoproliferative disease in a subject who is at risk of developing a lymphoproliferative disease, the method comprising administering to the subject an effective amount of a combination therapy consisting of:
   i) at least one autophagy inhibitor agent comprising chloroquine, or a pharmaceutically acceptable salt thereof; and
   ii) at least one CDK inhibitor agent comprising flavopiridol or a pharmaceutically acceptable salt thereof;
   in an amount sufficient to enhance the cytotoxicity of the combination relative to the CDK inhibitor agent treatment alone;
   wherein the subject has chronic lymphocytic leukemia (CLL).

2. The method of claim 1, wherein the CDK inhibitor agent is administered in a dosage amount that is less than that required for the CDK inhibitor agent as an individual therapy to elicit a comparable therapeutic effect.

3. The method of claim 1, wherein the autophagy inhibitor agent and the CDK inhibitor agent are administered separately.

4. The method of claim 1, comprising administering the CDK inhibitor agent in an amount effective to obtain a therapeutic effect, and the autophagy inhibitor agent in an amount effective to block any adverse effects mediated by the CDK inhibitor agent, but not to antagonize the therapeutic effect of the CDK inhibitor agent.

5. The method of claim 1, wherein the subject is refractory to other treatments.

6. The method of claim 1, wherein the subject is refractory to treatment with the CDK inhibitor agent alone.

7. The method of claim 1, wherein the subject is a human subject.

8. The method of claim 1, wherein at least the autophagy inhibitor agent is (co)administered in an amount ranging from about 0.1 µM to about a maximum tolerated dosage for the autophagy inhibitor.

9. The method of claim 1, wherein the autophagy inhibitor agent is (co)administered in an amount ranging from about 0.1 to about 0.5 µM.

10. The method of claim 1, wherein the combination is (co)administered parenterally, orally, intraperitoneally, intravenously, intraarterially, transdermally, intramuscularly, liposomally, via local delivery by catheter or stent, subcutaneously, intraadiposally, or intrathecally.

* * * * *

UNITED STATES PATENT AND TRADEMARK OFFICE
CERTIFICATE OF CORRECTION

PATENT NO. : 9,044,474 B2
APPLICATION NO. : 13/883862
DATED : June 2, 2015
INVENTOR(S) : John C. Byrd et al.

Page 1 of 1

It is certified that error appears in the above-identified patent and that said Letters Patent is hereby corrected as shown below:

In the Specification

Column 1, Lines 18-20 replace the Government Support Clause with:
--This invention was made with government support under grant number P01 CA081534 awarded by the National Institutes of Health. The government has certain rights in the invention.--

Signed and Sealed this
Fourth Day of August, 2020

Andrei Iancu
*Director of the United States Patent and Trademark Office*